United States Patent
Ratnam et al.

(10) Patent No.: US 12,160,298 B2
(45) Date of Patent: Dec. 3, 2024

(54) MULTI-ANTENNA WIFI BASED BREATHING RATE ESTIMATION

(71) Applicant: Samsung Electronics Co., Ltd., Suwon-si (KR)

(72) Inventors: Vishnu Vardhan Ratnam, Plano, TX (US); Hao Chen, Allen, TX (US); Abhishek Sehgal, Plano, TX (US); Hao-Hsuan Chang, Plano, TX (US)

(73) Assignee: Samsung Electronics Co., Ltd., Suwon-si (KR)

( * ) Notice: Subject to any disclaimer, the term of this patent is extended or adjusted under 35 U.S.C. 154(b) by 1 day.

(21) Appl. No.: 18/321,614

(22) Filed: May 22, 2023

(65) Prior Publication Data

US 2023/0387994 A1 Nov. 30, 2023

Related U.S. Application Data

(60) Provisional application No. 63/345,322, filed on May 24, 2022.

(51) Int. Cl.
*H04B 7/06* (2006.01)
*H04L 5/00* (2006.01)
(Continued)

(52) U.S. Cl.
CPC ......... *H04B 7/0626* (2013.01); *H04L 5/0048* (2013.01); *H04L 25/0202* (2013.01); *H04W 72/0446* (2013.01)

(58) Field of Classification Search
CPC .. H04B 7/0626; H04B 7/0695; H04B 7/0617; H04B 17/21; H04B 7/06952;
(Continued)

(56) References Cited

U.S. PATENT DOCUMENTS

2012/0052901 A1* 3/2012 Zhu ................. H04L 1/0031
455/517
2016/0022145 A1 1/2016 Mostov
(Continued)

FOREIGN PATENT DOCUMENTS

CN 106618497 A 5/2017
CN 106725488 A 5/2017
(Continued)

OTHER PUBLICATIONS

International Search Report and Written Opinion issued Aug. 28, 2023 regarding International Application No. PCT/KR2023/007099, 7 pages.
(Continued)

*Primary Examiner* — Khanh C Tran

(57) ABSTRACT

A method includes receiving CSI frames among P CSI frames transmitted from another electronic device. The method includes estimating a CSI from each of the received CSI frames as an available CSI estimate. The method includes identifying an impairment model accounting for inclusion of amplitude or phase errors of an estimated CSI corresponding to a p-th CSI frame among the P CSI frames. The method includes compensating, via the impairment model, for the errors in amplitude and phase of P CSI estimates. Compensating for the errors in amplitude and phase of the P CSI estimates can be based on: approximating a missing CSI estimate based on the available CSI estimates; determining an AGC gain value; or computing the errors in the phase based on a weighted least-squares solution. The method includes estimating a breathing rate of a subject based on different spatial dimensions of the P compensated CSI estimates.

20 Claims, 14 Drawing Sheets

(51) Int. Cl.
*H04L 25/02* (2006.01)
*H04W 72/0446* (2023.01)

(58) Field of Classification Search
CPC ..... H04B 7/0634; H04L 5/0048; H04L 5/005; H04L 5/0051; H04L 25/021; H04L 25/0202; H04L 25/0224; H04L 25/0228; H04W 72/0446; H04W 72/044
See application file for complete search history.

(56) References Cited

U.S. PATENT DOCUMENTS

| | | | |
|---|---|---|---|
| 2021/0022619 | A1 | 1/2021 | Ho et al. |
| 2021/0186369 | A1 | 6/2021 | Wei et al. |
| 2022/0095950 | A1 | 3/2022 | Cheng et al. |
| 2022/0202358 | A1 | 6/2022 | Ho et al. |
| 2022/0304051 | A1* | 9/2022 | Aboul-Magd ....... H04B 7/0626 |
| 2022/0322116 | A1* | 10/2022 | Aboul-Magd ....... H04W 24/08 |
| 2023/0112537 | A1 | 4/2023 | Sakamoto et al. |
| 2023/0388840 | A1* | 11/2023 | Au .......................... G01S 13/56 |
| 2023/0397824 | A1 | 12/2023 | Yang et al. |
| 2024/0129779 | A1* | 4/2024 | Au ....................... H04L 5/0051 |

FOREIGN PATENT DOCUMENTS

| | | |
|---|---|---|
| CN | 109330597 A | 2/2019 |
| CN | 109998549 A | 7/2019 |
| CN | 112386236 A | 2/2021 |
| CN | 113743374 A | 12/2021 |
| CN | 114999643 A | 9/2022 |
| CN | 115002822 A | 9/2022 |
| CN | 115040109 A | 9/2022 |
| CN | 115299917 A | 11/2022 |
| CN | 115474901 A | 12/2022 |
| CN | 115481652 A | 12/2022 |
| EP | 3492944 A1 | 6/2019 |
| JP | 2019179020 A | 10/2019 |
| WO | 2010134933 A1 | 11/2010 |
| WO | 2017156492 A1 | 9/2017 |
| WO | 2022095869 A1 | 5/2022 |

OTHER PUBLICATIONS

Fang et al., "A novel sleep respiratory rate detection method for obstructive sleep apnea based on characteristic moment waveform," Journal of Healthcare Engineering, vol. 2018, Article ID 1902176, Jan. 2018, 11 pages.

Charlton et al., "Breathing rate estimation from the electrocardiogram and photoplethysmogram: A review," IEEE Reviews in Biomedical Engineering, vol. 11, Oct. 2018, pp. 2-20, 19 pages.

Regev et al., "Radar-based, simultaneous human presence detection and breathing rate estimation," Sensors, vol. 21, No. 10, May 2021, 16 pages.

Natarajan et al., "Measurement of respiratory rate using wearable devices and applications to covid-19 detection," npj Digital Medicine, vol. 4, Article No. 136, Sep. 2021, 10 pages.

Park et al., "Single channel receiver limitations in Doppler radar measurements of periodic motion," 2006 IEEE Radio and Wireless Symposium, pp. 99-102, Oct. 2006, 4 pages.

Droitcour et al., "Signal-to-noise ratio in doppler radar system for heart and respiratory rate measurements," IEEE Transactions on Microwave Theory and Techniques, vol. 57, No. 10, pp. 2498-2507, Oct. 2009, 10 pages.

Salmi et al., "Propagation parameter estimation, modeling and measurements for UltraWideBand MIMO radar," IEEE Transactions on Antennas and Propagation, vol. 59, No. 11, pp. 4257-4267, Nov. 2011, 11 pages.

Adib et al., "Smart Homes That Monitor Breathing and Heart Rate," Proceedings of the 33rd Annual ACM Conference on Human Factors in Computing Systems, Apr. 2015, p. 837-846, 10 pages.

Patwari et al., "Breathfinding: A wireless network that monitors and locates breathing in a home," IEEE Journal of Selected Topics in Signal Processing, vol. 8, No. 1, pp. 30-42, Nov. 2013, 14 pages.

Abdelnasser et al., "UbiBreathe: A Ubiquitous non-Invasive WiFi-based breathing estimator," Proceedings of the 16th ACM International Symposium on Mobile Ad Hoc Networking and Computing, pp. 277-286, Jun. 2015, 10 pages.

Liu et al., "Wi-sleep: Contactless sleep monitoring via WiFi signals," 2014 IEEE Real-Time Systems Symposium, pp. 346-355, Dec. 2014, 10 pages.

Liu et al., "Tracking vital signs during sleep leveraging off-the-shelf wifi," Proceedings of the 16th ACM International Symposium on Mobile Ad Hoc Networking and Computing, Jun. 2015, p. 267-276, 10 pages.

Wang et al., "Tensorbeat: Tensor decomposition for monitoring multi-person breathing beats with commodity WiFi," ACM Transactions on Intelligent Systems and Technology, vol. 9, No. 1, Sep. 2017, 27 pages.

Zeng et al., "Fullbreathe: Full human respiration detection exploiting complementarity of csi phase and amplitude of wifi signals," Proceedings of the ACM on Interactive, Mobile, Wearable and Ubiquitous Technologies, vol. 2, No. 3, pp. 1-19, Sep. 2018, 19 pages.

Chen et al., "Tr-breath: Time-reversal breathing rate estimation and detection," IEEE Transactions on Biomedical Engineering, vol. 65, No. 3, pp. 489-501, Mar. 2018, 13 pages.

Dou et al., "Full respiration rate monitoring exploiting doppler information with commodity wi-fi devices," Sensors, vol. 21, No. 10, May 2021, 22 pages.

Wang et al., "Human respiration detection with commodity WiFi devices: do user location and body orientation matter?," Proceedings of the 2016 ACM International Joint Conference on Pervasive and Ubiquitous Computing, pp. 25-36, Sep. 2016, 12 pages.

\* cited by examiner

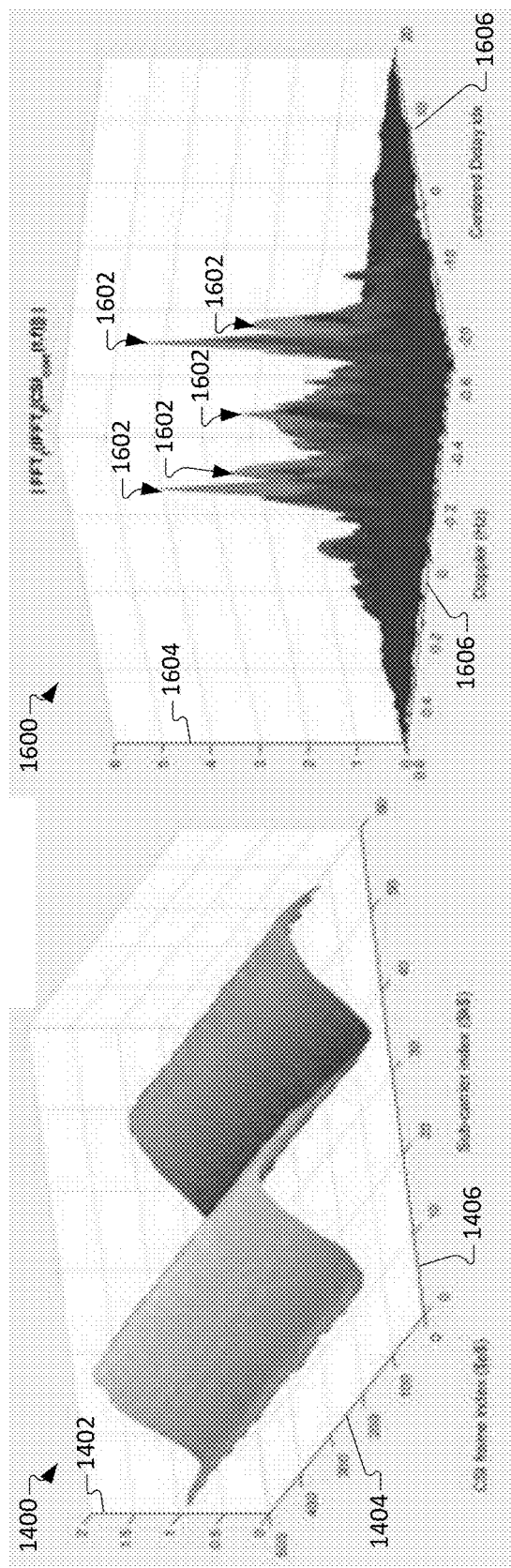
FIG. 14
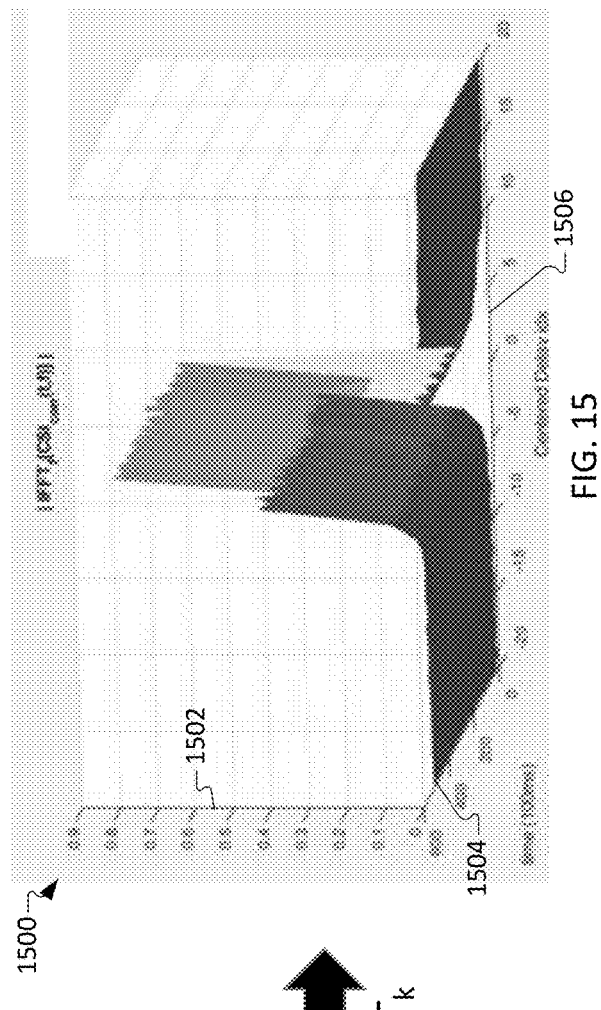
FIG. 15
FIG. 16
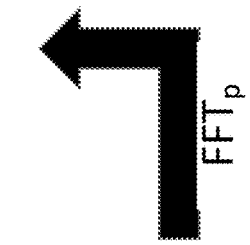
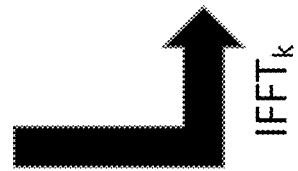

MULTI-ANTENNA WIFI BASED BREATHING RATE ESTIMATION

CROSS-REFERENCE TO RELATED APPLICATION(S) AND CLAIM OF PRIORITY

This application claims priority under 35 U.S.C. § 119(e) to U.S. Provisional Patent Application No. 63/345,322 filed on May 24, 2022. The above-identified provisional patent application is hereby incorporated by reference in its entirety.

TECHNICAL FIELD

This disclosure relates generally to wireless communication systems. More specifically, this disclosure relates to multi-antenna WiFi-based breathing rate estimation.

BACKGROUND

Breathing rate of a person is a vital sign. The breathing rate of a person can be a parameter for realizing many technical use-cases. Beyond the use-cases of numerous health applications such as sleep quality detection, sleep apnea, asthma diagnosis etc., a parameter corresponding to the breathing rate of a person can also be used for detection of human presence and monitoring in home security. The increase in demand for such health-monitoring has also led to an expanding market for wearable devices ("wearables"). Although such wearables can accurately measure the breathing rate, they are often expensive, and can be intrusive and uncomfortable. Furthermore, wearables cannot be used for some use-cases such as in detection of human presence or home security monitoring. Correspondingly, there has been an increased interest recently in wireless breathing rate monitoring. In such solutions, there is a transmitter (TX) that periodically transmits a known wireless signal into a channel which includes the subject performing breathing. The receiver (RX) estimates the channel response from the received signal and then observes its temporal variation to predict the breathing rate of the subject, a task referred to as wireless sensing. In some methods, a monostatic RADAR is used both as the TX and as the RX estimating the channel. However, use of such specialized RADAR equipment requires an additional deployment of a RADAR system and may impose additional cost burdens especially in household scenarios.

SUMMARY

This disclosure provides multi-antenna WiFi-based breathing rate estimation.

In one embodiment, a method for estimating a breathing rate based on multi-antenna WiFi signals is provided. the method includes receiving, by a transceiver that includes N receive (Rx) antennas, channel state information (CSI) frames among P CSI frames transmitted from M transmit (Tx) antennas of another electronic device. The method includes estimating, by a processor of an electronic device operably connected to the transceiver, a CSI from each of the received CSI frames as an available CSI estimate. The method includes identifying an impairment model to account for inclusion of one or more errors in an amplitude or a phase of an estimated CSI that is indexed by p and that corresponds to a p-th CSI frame among the P CSI frames. The method includes compensating, via the impairment model, for the one or more errors in the amplitude and the phase of P CSI estimates. Compensating for the one or more errors in the amplitude and the phase of the P CSI estimates includes performing at least one of: approximating a missing CSI estimate corresponding to a missing CSI frame among P CSI frames based on the available CSI estimates; determining at least one automatic gain control (AGC) gain value; or computing the one or more errors in the phase based on a weighted least-squares solution. The method includes estimating a breathing rate of a subject based on different spatial dimensions of the P compensated CSI estimates.

In another embodiment, an electronic device for estimating a breathing rate based on multi-antenna WiFi signals is provided. The electronic device includes a transceiver that includes N receive (Rx) antennas; and a processor operably connected to the transceiver. The processor is configured to receive channel state information (CSI) frames among P CSI frames transmitted from M transmit (Tx) antennas of another electronic device. The processor is configured to estimate a CSI from each of the received CSI frames as an available CSI estimate.

The processor is configured to identify an impairment model to account for inclusion of one or more errors in an amplitude or a phase of an estimated CSI that is indexed by p and that corresponds to a p-th CSI frame among the P CSI frames. The processor is configured to compensate, via the impairment model, for the one or more errors in the amplitude and the phase of P CSI estimates, wherein to compensate for the one or more errors in the amplitude and the phase of the P CSI estimates. The processor is further configured to perform at least one of: approximate a missing CSI estimate corresponding to a missing CSI frame among P CSI frames based on the available CSI estimates; determine at least one automatic gain control (AGC) gain value; or compute the one or more errors in the phase based on a weighted least-squares solution. The processor is configured to estimate a breathing rate of a subject based on different spatial dimensions of the P compensated CSI estimates.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B. Further, as used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Definitions for other certain words and phrases may be provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 14 illustrates compensated CSI in which there are no residual errors and no corrupted samples are identified, according to embodiments of this disclosure;

FIG. 15 illustrates an Inverse Fast Fourier Transform of the compensated CSI of FIG. 14, according to embodiments of this disclosure;

FIG. 16 illustrates an example Doppler spectrum as a Fourier Transform over the time domain of the compensated CSI of FIG. 15 containing peaks corresponding to the frequency of breathing of the subject, according to embodiments of this disclosure;

DETAILED DESCRIPTION

Figure 1:
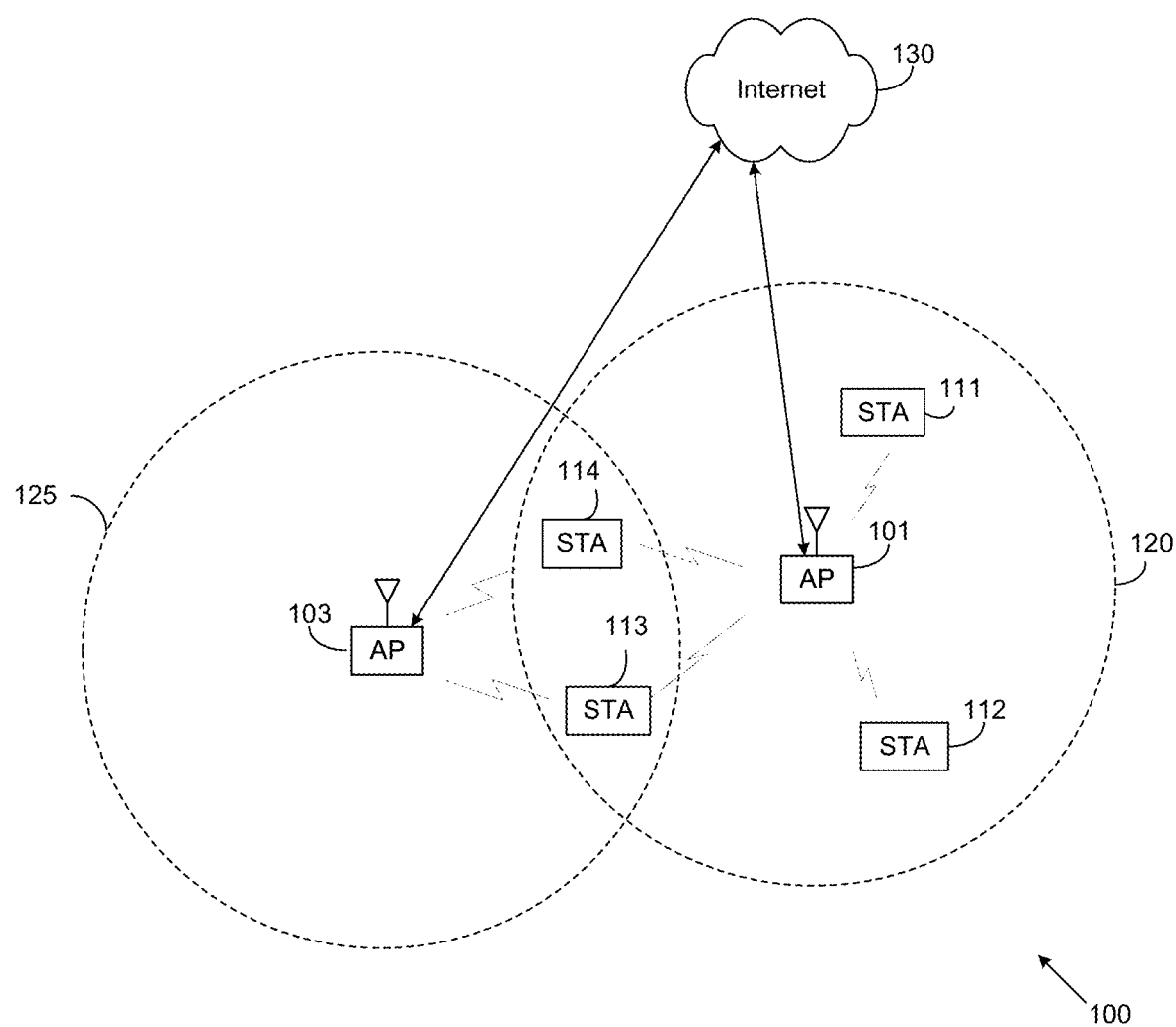
FIG. 1 illustrates an example wireless network according to this disclosure.

FIGS. 1 through 18, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably-arranged wireless communication system.

As introduced above, a RADAR system for wirelessly monitoring the breathing rate of a person imposes cost burdens onto a household that is required to obtain the RADAR equipment. In alternative methods, existing wireless architecture, such as commodity WiFi, is used for performing breathing rate detection, where time/frequency synchronization between TX and RX may not exist. In general, a household is already equipped with WiFi equipment, such as an access point (AP), and the WiFi-equipped household is not required to obtain additional equipment (for example, hardware for a RADAR system).

Due to the low cost and wide-scale deployment of commodity WiFi, such a commodity WiFi system is an attractive solution for estimation of a subject's breathing rate. As an example only, the subject is a person in the examples described in this disclosure, however, it is understood that the subject can be another breathing body in other examples. The WiFi systems are not error-free. Due to lack of synchronization between the WiFi transmitter and WiFi receiver, and due to the effects of automatic gain control (AGC), etc., the channel state information (CSI) obtained from such WiFi systems suffer from errors in amplitude and phase. Additionally, some packets can be missed by the WiFi receiver, and as a result the CSI may be unavailable to the WiFi receiver. These errors can degrade the accuracy of the estimation of the subject's breathing rate as detected and/or measured at the WiFi receiver. To overcome these problems, embodiments of this disclosure provide CSI pre-processing methods to remove such errors at the WiFi receiver. In addition, some modern WiFi devices are equipped with multiple antenna elements, and as a result, CSI from multiple antennas may be available at the WiFi receiver. Embodiments of this disclosure provide methods to combine the CSI from multiple antennas at the RX to accurately estimate the breathing rate of the subject.

As introduced above, in order to determine a subject's breathing rate vital sign, embodiments of this disclosure include methods to use CSI obtained from multi-antenna WiFi infrastructure for performing the breathing rate estimation. Embodiments of this disclosure develop a detailed system model (for example, a mathematical system model) that takes into consideration the errors in the CSI amplitude and the errors in the CSI phase. Embodiments of this disclosure provide a methodology for compensating for these amplitude and phase errors to "clean" (for example, reduce/remove errors from, and thereby reconstruct) the CSI. Embodiments of this disclosure provide several different methods for estimating the subject's breathing rate from the cleaned CSI (e.g., cleaned multi-antenna CSI). In particular, these methods utilize the different spatial dimensions of the cleaned CSI for estimating the breathing rate of a subject. The algorithms provided according to embodiments of this disclosure are then evaluated compared to data obtained from a real WiFi testing environment (e.g., WiFi test-bed) under several different scenarios. The testing results show a 50% reduction in both the estimation root-mean-squared-error and in the misdetection probability, in comparison to existing conventional solutions.

This disclosure provides methods to compensate (e.g., "clean") multi-antenna WiFi CSI, and then use the compensated multi-antenna WiFi CSI for performing breathing rate estimation of a subject (e.g., a person breathing in a vicinity of the WiFi device). This breathing rate estimation can have numerous applications, such as monitoring biological signals of subject for medical purposes, detecting occupancy of a room, detecting number of subjects in a room, for generating intruder alarms, etc.

FIG. 1 illustrates an example wireless network 100 according to various embodiments of the present disclosure. The embodiment of the wireless network 100 shown in FIG. 1 is for illustration only. Other embodiments of the wireless network 100 could be used without departing from the scope of this disclosure.

The wireless network 100 includes access points (APs) 101 and 103. The APs 101 and 103 communicate with at least one network 130, such as the Internet, a proprietary Internet Protocol (IP) network, or other data network. The AP 101 provides wireless access to the network 130 for a plurality of stations (STAs) 111-114 within a coverage area 120 of the AP 101. The APs 101-103 may communicate with each other and with the STAs 111-114 using WI-FI or other WLAN communication techniques.

Depending on the network type, other well-known terms may be used instead of "access point" or "AP," such as "router" or "gateway." For the sake of convenience, the term "AP" is used in this disclosure to refer to network infrastructure components that provide wireless access to remote terminals. In WLAN, given that the AP also contends for the wireless channel, the AP may also be referred to as a STA. Also, depending on the network type, other well-known terms may be used instead of "station" or "STA," such as "mobile station," "subscriber station," "remote terminal," "user equipment," "wireless terminal," or "user device." For the sake of convenience, the terms "station" and "STA" are used in this disclosure to refer to remote wireless equipment that wirelessly accesses an AP or contends for a wireless channel in a WLAN, whether the STA is a mobile device (such as a mobile telephone or smartphone) or is normally considered a stationary device (such as a desktop computer, AP, media player, stationary sensor, television, etc.).

Dotted lines show the approximate extents of the coverage areas 120 and 125, which are shown as approximately circular for the purposes of illustration and explanation only. It should be clearly understood that the coverage areas associated with APs, such as the coverage areas 120 and 125, may have other shapes, including irregular shapes, depending upon the configuration of the APs and variations in the radio environment associated with natural and man-made obstructions.

As described in more detail below, one or more of the APs may include circuitry and/or programming for estimating a breathing rate based on multi-antenna WiFi signals in WLANs. Although FIG. 1 illustrates one example of a wireless network 100, various changes may be made to FIG. 1. For example, the wireless network 100 could include any number of APs and any number of STAs in any suitable arrangement. Also, the AP 101 could communicate directly with any number of STAs and provide those STAs with wireless broadband access to the network 130. Similarly, each AP 101-103 could communicate directly with the network 130 and provide STAs with direct wireless broadband access to the network 130. Further, the APs 101 and/or 103 could provide access to other or additional external networks, such as external telephone networks or other types of data networks.

Figure 2A:
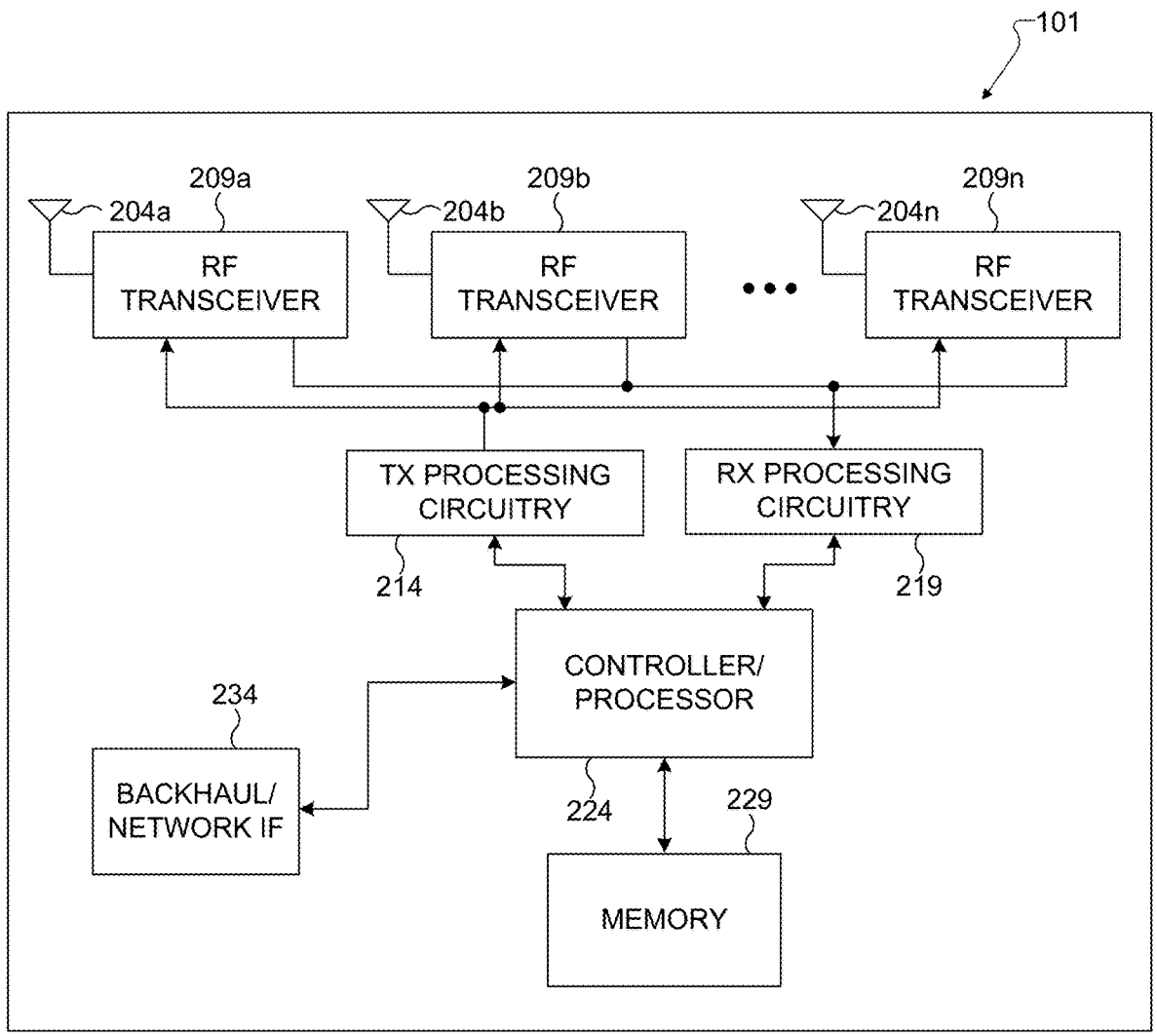
FIG. 2A illustrates an example access point (AP) according to this disclosure.

FIG. 2A illustrates an example AP 101 according to various embodiments of the present disclosure. The embodiment of the AP 101 illustrated in FIG. 2A is for illustration only, and the AP 103 of FIG. 1 could have the same or similar configuration. However, APs come in a wide variety of configurations, and FIG. 2A does not limit the scope of this disclosure to any particular implementation of an AP.

The AP 101 includes multiple antennas 204a-204n, multiple RF transceivers 209a-209n, transmit (TX) processing circuitry 214, and receive (RX) processing circuitry 219. The AP 101 also includes a controller/processor 224, a memory 229, and a backhaul or network interface 234. The RF transceivers 209a-209n receive, from the antennas 204a-204n, incoming RF signals, such as signals transmitted by STAs in the network 100. The RF transceivers 209a-209n down-convert the incoming RF signals to generate IF or baseband signals. The IF or baseband signals are sent to the RX processing circuitry 219, which generates processed baseband signals by filtering, decoding, and/or digitizing the baseband or IF signals. The RX processing circuitry 219 transmits the processed baseband signals to the controller/processor 224 for further processing.

The TX processing circuitry 214 receives analog or digital data (such as voice data, web data, e-mail, or interactive video game data) from the controller/processor 224. The TX processing circuitry 214 encodes, multiplexes, and/or digitizes the outgoing baseband data to generate processed baseband or IF signals. The RF transceivers 209a-209n receive the outgoing processed baseband or IF signals from the TX processing circuitry 214 and up-converts the baseband or IF signals to RF signals that are transmitted via the antennas 204a-204n.

The controller/processor 224 can include one or more processors or other processing devices that control the overall operation of the AP 101. For example, the controller/processor 224 could control the reception of forward channel signals and the transmission of reverse channel signals by the RF transceivers 209a-209n, the RX processing circuitry 219, and the TX processing circuitry 214 in accordance with well-known principles. The controller/processor 224 could support additional functions as well, such as more advanced wireless communication functions. For instance, the controller/processor 224 could support beam forming or directional routing operations in which outgoing signals from multiple antennas 204a-204n are weighted differently to effectively steer the outgoing signals in a desired direction. The controller/processor 224 could also support OFDMA operations in which outgoing signals are assigned to different subsets of subcarriers for different recipients (e.g., different STAs 111-114). Any of a wide variety of other functions could be supported in the AP 101 by the controller/processor 224 including estimating a breathing rate based on multi-antenna WiFi signals. In some embodiments, the controller/processor 224 includes at least one microprocessor or microcontroller. The controller/processor 224 is also capable of executing programs and other processes resident in the memory 229, such as an OS. The controller/processor 224 can move data into or out of the memory 229 as required by an executing process.

The controller/processor 224 is also coupled to the backhaul or network interface 234. The backhaul or network interface 234 allows the AP 101 to communicate with other devices or systems over a backhaul connection or over a network. The interface 234 could support communications over any suitable wired or wireless connection(s). For example, the interface 234 could allow the AP 101 to communicate over a wired or wireless local area network or over a wired or wireless connection to a larger network (such as the Internet). The interface 234 includes any suitable structure supporting communications over a wired or wireless connection, such as an Ethernet or RF transceiver. The memory 229 is coupled to the controller/processor 224. Part of the memory 229 could include a RAM, and another part of the memory 229 could include a Flash memory or other ROM.

As described in more detail below, the AP 101 may include circuitry and/or programming for estimating a breathing rate based on multi-antenna WiFi signals. Although FIG. 2A illustrates one example of AP 101, various changes may be made to FIG. 2A. For example, the AP 101 could include any number of each component shown in FIG. 2A. As a particular example, an access point could include a number of interfaces 234, and the controller/processor 224 could support routing functions to route data between different network addresses. As another particular example, while shown as including a single instance of TX processing circuitry 214 and a single instance of RX processing circuitry 219, the AP 101 could include multiple instances of each (such as one per RF transceiver). Alternatively, only one antenna and RF transceiver path may be included, such as in legacy APs. Also, various components in FIG. 2A could be combined, further subdivided, or omitted and additional components could be added according to particular needs.

Figure 2B:
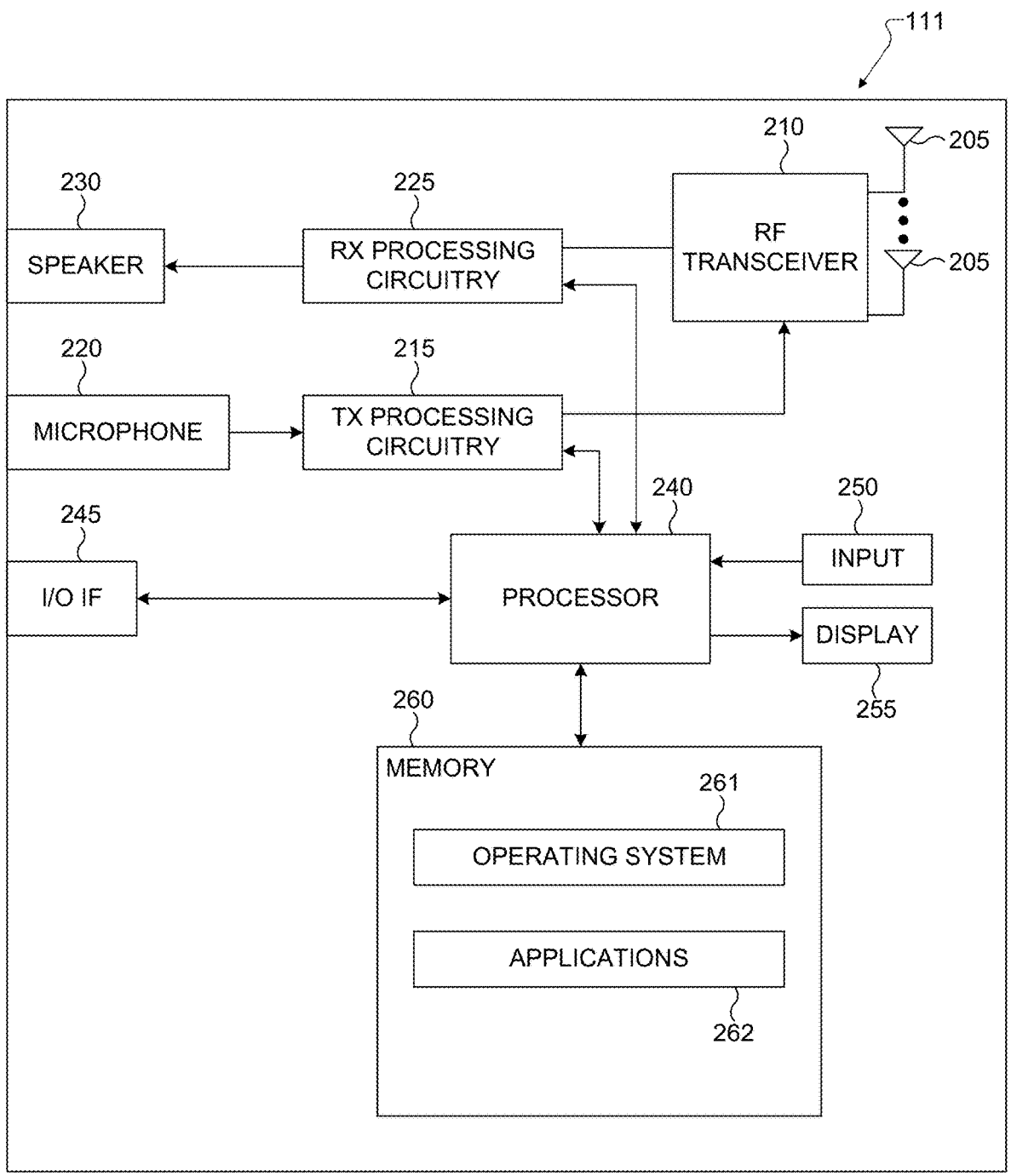
FIG. 2B illustrates an example station (STA) according to this disclosure.

FIG. 2B illustrates an example STA 111 according to various embodiments of this disclosure. The embodiment of the STA 111 illustrated in FIG. 2B is for illustration only, and the STAs 111-115 of FIG. 1 could have the same or similar configuration. However, STAs come in a wide variety of configurations, and FIG. 2B does not limit the scope of this disclosure to any particular implementation of a STA.

The STA 111 includes antenna(s) 205, a radio frequency (RF) transceiver 210, TX processing circuitry 215, a microphone 220, and receive (RX) processing circuitry 225. The STA 111 also includes a speaker 230, a controller/processor 240, an input/output (I/O) interface (IF) 245, a touchscreen 250, a display 255, and a memory 260. The memory 260 includes an operating system (OS) 261 and one or more applications 262.

The RF transceiver 210 receives, from the antenna(s) 205, an incoming RF signal transmitted by an AP of the network 100. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the controller/processor 240 for further processing (such as for web browsing data).

The TX processing circuitry 215 receives analog or digital voice data from the microphone 220 or other outgoing baseband data (such as web data, e-mail, or interactive video game data) from the controller/processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna(s) 205.

The controller/processor 240 can include one or more processors and execute the basic OS program 261 stored in the memory 260 in order to control the overall operation of the STA 111. In one such operation, the main controller/processor 240 controls the reception of forward channel signals and the transmission of reverse channel signals by the RF transceiver 210, the RX processing circuitry 225, and the TX processing circuitry 215 in accordance with well-known principles. The main controller/processor 240 can also include processing circuitry configured for estimating a breathing rate based on multi-antenna WiFi signals. In some embodiments, the controller/processor 240 includes at least one microprocessor or microcontroller.

The controller/processor 240 is also capable of executing other processes and programs resident in the memory 260, such as operations for estimating a breathing rate based on multi-antenna WiFi signals. The controller/processor 240 can move data into or out of the memory 260 as required by an executing process. In some embodiments, the controller/processor 240 is configured to execute a plurality of applications 262, such as applications for jointly estimating a breathing rate based on multi-antenna WiFi signals. The controller/processor 240 can operate the plurality of applications 262 based on the OS program 261 or in response to a signal received from an AP. The main controller/processor 240 is also coupled to the I/O interface 245, which provides STA 111 with the ability to connect to other devices such as laptop computers and handheld computers. The I/O interface 245 is the communication path between these accessories and the main controller 240.

The controller/processor 240 is also coupled to the touchscreen 250 and the display 255. The operator of the STA 111 can use the touchscreen 250 to enter data into the STA 111. The display 255 may be a liquid crystal display, light emitting diode display, or other display capable of rendering text and/or at least limited graphics, such as from web sites. The memory 260 is coupled to the controller/processor 240. Part of the memory 260 could include a random access memory (RAM), and another part of the memory 260 could include a Flash memory or other read-only memory (ROM).

Although FIG. 2B illustrates one example of STA 111, various changes may be made to FIG. 2B. For example, various components in FIG. 2B could be combined, further subdivided, or omitted and additional components could be added according to particular needs. In particular examples, the STA 111 may include any number of antenna(s) 205 for MIMO communication with an AP 101. In another example, the STA 111 may not include voice communication or the controller/processor 240 could be divided into multiple processors, such as one or more central processing units (CPUs) and one or more graphics processing units (GPUs). Also, while FIG. 2B illustrates the STA 111 configured as a mobile telephone or smartphone, STAs could be configured to operate as other types of mobile or stationary devices.

Figure 3:
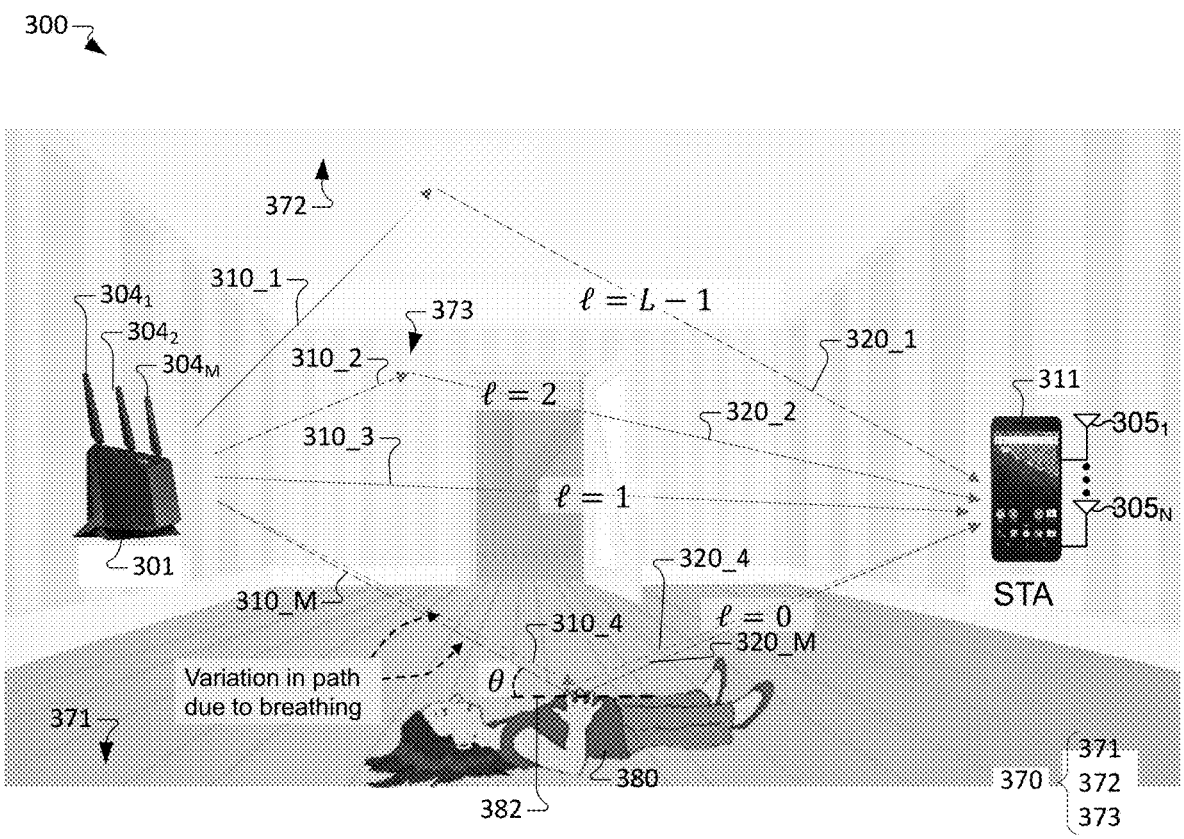
FIG. 3 illustrates an example wireless communication system performing breathing rate estimation to determine a breathing rate vital sign of a subject in an environment, in accordance with an embodiment of this disclosure.

FIG. 3 illustrates an example wireless communication system 300 performing breathing rate estimation to determine a breathing rate vital sign of a subject in an environment, in accordance with an embodiment of this disclosure. Particularly, the system 300 is composed of an AP 301 and a STA 311 located in an environment 370, and the system 300 performs breathing rate estimation to determine the breathing rate vital sign of the subject 380 located in the environment 370. The embodiment of the wireless communication system 300 shown in FIG. 3 is for illustration only, and other embodiments could be used without departing from the scope of this disclosure. For example, the embodiment of the wireless communication system 300 shown in FIG. 3 could have the same or similar configuration as the network 100 of FIG. 1. The AP 301 and STA 311 of FIG. 3 can have the same or similar configuration as the AP 201 of FIG. 2A and the STA 111 of FIG. 2B, respectively. The Mtransmitting antennas $304_1$-$304_M$ of the AP 301 can represent antennas of the AP 201 of FIG. 2A. The STA 311 includes N receive (Rx) antennas, including first antenna $305_1$ through N-th antenna $305_N$, which can represent antenna(s) 205 of the STA 111 of FIG. 2B. The system 300 includes MN antenna pairs composed from the N Rx antennas respectively paired with each of the M Tx antennas, and each of the MN antenna pairs indexed by m.

For simplicity, commodity Wi-Fi infrastructure can refer to the AP 301, the STA 311, or the system 300 that includes both the AP 301 and the STA 311. The commodity Wi-Fi infrastructure can be modern WiFi devices equipped with multiple antenna elements. Three main features of the commodity Wi-Fi infrastructure according to embodiments of this disclosure will be described, including the features of: (1) obtaining CSI from multi-antenna commodity Wi-Fi infrastructure to estimate a breathing rate of the subject 380 based on a system model that is configured to take account for one or more errors in CSI amplitude and one or more errors in the CSI phase; (2) compensating for the one or more errors in the CSI amplitude and the one or more errors in the CSI phase to reconstruct the CSI; and (3) estimating the subject's 380 breathing rate from the reconstructed multi-antenna CSI based on different spatial dimensions of the reconstructed CSI.

As an example, the subject 380, whose breathing rate $f_{br}$ (in Hz) will be estimated, is in the vicinity of the STA 311. The subject 380 is relatively stationary or slowly-moving, for example, the subject can be lying on the floor 371 facing the ceiling 372.

In the scenario shown, AP 301 transmits to the STA 311 (as receiver) a signal 310_1 through 310_M, such as a CSI frame p, from each of the M Tx antennas. Some of the transmitted signals reflect off a stationary surface of object in the environment 370, such as a ceiling, wall, floor, or furniture. For example, the signal 310_1 transmitted by Tx antenna $304_1$ reflects off the ceiling 372; and the signal 310_2 transmitted by Tx antenna 3042 reflects off a wall 373. As a result, the STA 311 receives reflected signals 320_1 and 320_2, respectively. Some of the transmitted signals reflect off a moving surface of the subject 380 in the environment 370, such as the moving torso (i.e., chest) of a breathing person. For example, the signals 310_4 and 10_M transmitted by the AP 311 are incident upon the moving surface of the subject's 380 torso at an angle θ, relative to a surface plane 382 of the torso. As a result, the STA 311 receives reflected signals 320_4 and 320_M, respectively.

The surface plane 382 of the subject's 380 torso can be parallel to the surface of the floor 371 when the subject lies flat on the floor 371. Some of the transmitted signals 310_3 are received by the STA 311 without being reflected at any surface.

Although FIG. 3 illustrates an example environment 370 within which a wireless communication system 300 estimates a subject's 380 breathing rate, various changes may be made to FIG. 3. Particularly, the presence of only one subject 380 is for simplicity and ease of explanation as an example only, but is not a limitation on the embodiments presented in this disclosure. Multiple subjects 380 can be present in the environment, and the system 300 can estimate their breathing rates, respectively. As another particular example, in one embodiment the transmitter can be an AP and the receiver can be a WiFi STA, or vice versa in another embodiment. For simplicity, the examples used in this disclosure refer to an embodiment in which the AP 301 is also referred to as the transmitter 301, and the STA 311 is also referred to as the receiver 311.

Figure 4:
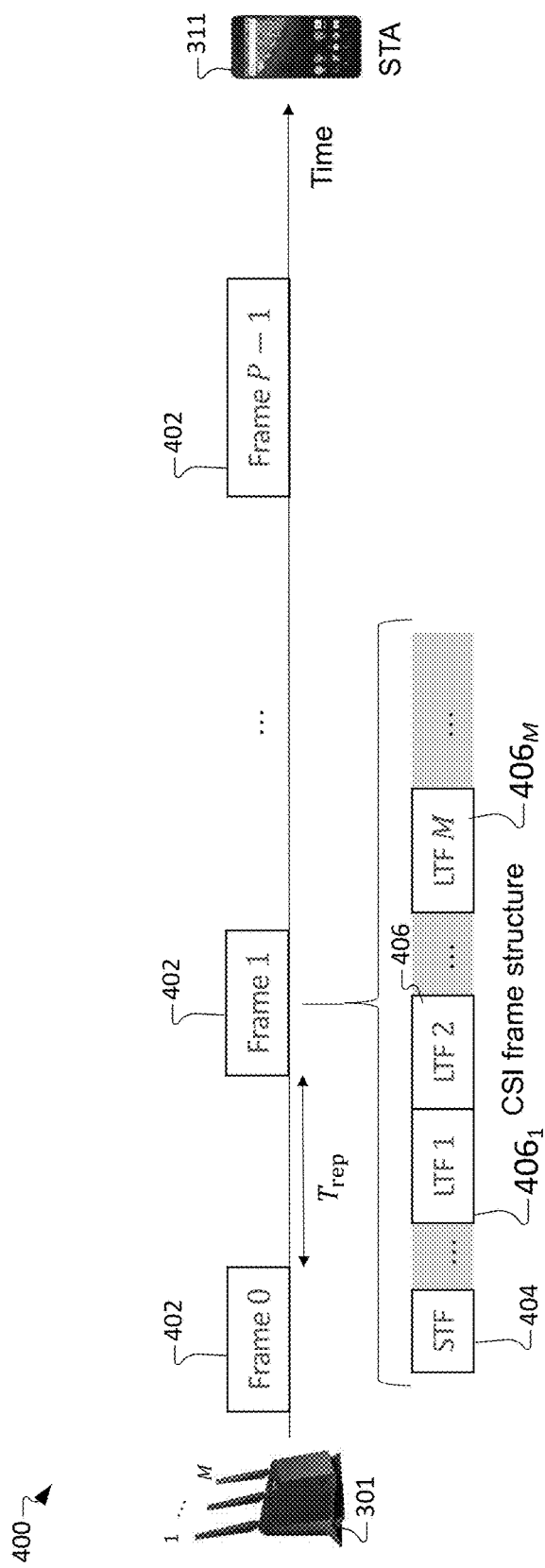
FIG. 4 illustrates an example of channel state information (CSI) frame transmission, in accordance with an embodiment of this disclosure.

FIG. 4 illustrates an example channel state information (CSI) frame transmission 400, in accordance with an embodiment of this disclosure. The embodiment of the CSI frame transmission shown in FIG. 4 is for illustration only, and other embodiments could be used without departing from the scope of this disclosure.

To enable estimation of the breath rate $f_{br}$ of the subject 380, the transmitter may transmit a sequence of WiFi channel state information (CSI) acquisition frames 402, that are transmitted periodically at an interval of $T_{rep}$ seconds each. The sequence of WiFi CSI acquisition frames includes P CSI frames 402 having a frame index p in a range from 0 through P−1. For ease of explanation, the CSI frame p is the p-th CSI frame.

In one embodiment, each CSI frame 402 can contain a short training field (STF) 404 and multiple pilot symbols 406, one pilot symbol transmitted from each of the M TX antennas of the AP 301 to help the STA 311 obtain the CSI from each of the M TX antennas. For example, the first TX antenna $304_1$ transmits the first pilot symbol $406_1$, which is illustrated as long training field (LTF) 1. Similarly, the M-th TX antenna $304_M$ transmits the M-th pilot symbol $406_M$ (illustrated as LTF M). In one embodiment, these CSI frames 402 can be beacon frames or null data packets, and the transmission can be using orthogonal frequency division multiplexing (OFDM) over K sub-carriers indexed as: $\mathcal{K} = \{1, \ldots, K\}$.

Using the received signal for each CSI frame p, the STA 311 obtains the corresponding MN×1 noisy CSI (from each TX antenna to each RX antenna) on sub-carrier k as a vectorized channel $\widetilde{\mathcal{H}}_{p,k}$. To avoid loss of generality, this disclosure describes a vectorization of the CSI where the z-th component of the MN×1 vector (i.e., $[\widetilde{\mathcal{H}}_{p,k}]_z$) represents the CSI between the TX antenna: $\lfloor z/N \rfloor + 1$ and RX antenna: $\mathrm{mod}\{z, N\}+1$.

Figure 5:
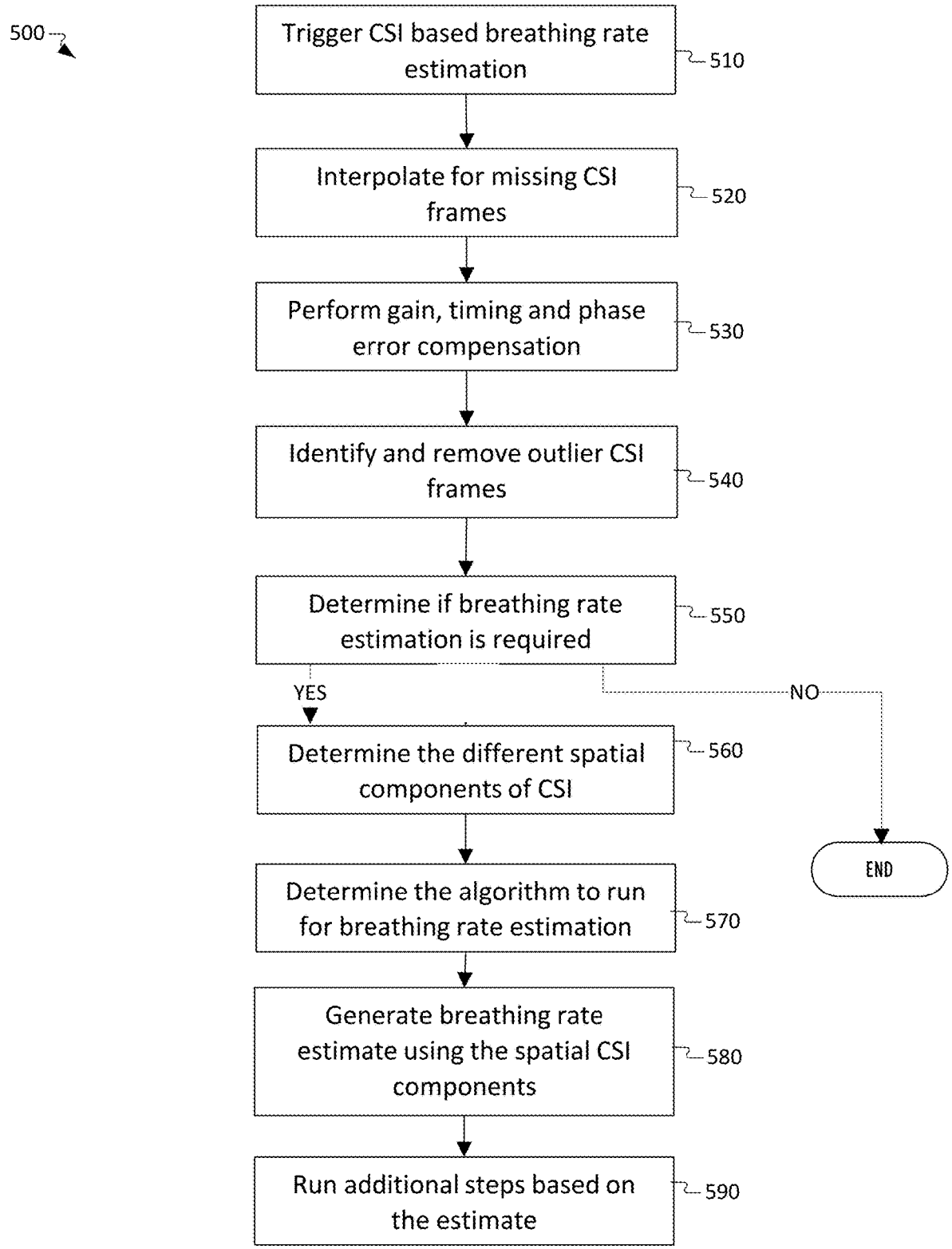
FIG. 5 illustrates an example method 500 for multi-antenna WiFi CSI-based breathing rate estimation, according to embodiments of the present disclosure.

FIG. 5 illustrates an example method 500 for multi-antenna WiFi CSI-based breathing rate estimation, according to embodiments of the present disclosure. The embodiment of the method 500 for multi-antenna WiFi CSI-based breathing rate estimation shown in FIG. 5 is for illustration only, and other embodiments (for example, the method 1800 of FIG. 18) could be used without departing from the scope of this disclosure.

At block 510, a trigger from a timer, external source or another CSI-based algorithm is used to trigger breathing rate estimation. To obtain an estimate the breathing rate of the subject 380, the receiver 311 may use the CSI estimates obtained from the previous P CSI frames: $\{\widetilde{\mathcal{H}}_{0,k}, \widetilde{\mathcal{H}}_{1,k}, \ldots, \widetilde{\mathcal{H}}_{P-1,k} | k \in \mathcal{K}\}$. However, firstly, due to the uncertainty of reception of frames, the CSI estimate obtained $\widetilde{\mathcal{H}}_{p,k}$ for some frame p can be missing. At block 520, the interpolation for missing CSI frames is performed. Secondly, due to synchronization errors and hardware impairments, the obtained CSI can be noisy and/or erroneous. These errors are compensated out of the obtained CSI (at blocks 520-570) before the breathing signal is estimated (at block 580), particularly by executing the CSI pre-processing methods according to embodiments of the present disclosure to remove such errors at the receiver.

Now refer back to block 520. Sometimes, when the AP 301 transmits P CSI frames, the STA 311 fails to receive one or more of the P CSI frames transmitted, which are referred to as one or more missing CSI frames. From among the P CSI frames transmitted, the STA 311 successfully receives some of the CSI frames, which are referred to as received CSI frames. As part of performing channel estimation, the STA 311 estimates a CSI from each of the received CSI frames, and such CSI estimate is referred to as an available CSI estimate. That is, a received CSI frame is available to be processed through a channel estimation algorithm yielding the available CSI estimate.

Embodiments of this disclosure identifies (e.g., generates) an impairment model to account for (e.g., identify; measure; quantify) inclusion of errors in an amplitude or a phase of the estimated CSI that is indexed by p and that corresponds to a p-th CSI frame among the P CSI frames. The missing CSI frames cause some of the errors accounted for in the impairment model.

For any missing CSI frame indexed by p, the preceding and succeeding CSI frames for which CSI is available and that are closest to the missing CSI frame are determined as $p=q_1$ and $p=q_2$, respectfully. A preceding available CSI estimate $\widetilde{\mathcal{H}}_{q_1,k}$ corresponds to the preceding CSI frame ($p=q_1$). A succeeding available CSI estimate $\widetilde{\mathcal{H}}_{q_2,k}$ corresponds to the succeeding CSI frame ($p=q_2$). Based on these preceding and succeeding available CSI estimates $\widetilde{\mathcal{H}}_{q_1,k}$, and $\widetilde{\mathcal{H}}_{q_2,k}$, the STA 311 approximates a missing CSI estimate corresponding to a missing CSI frame among P CSI frames. In one embodiment, the missing CSI estimate can be approximated as equivalent to the preceding available CSI estimate $\widetilde{\mathcal{H}}_{q_1,k}$ corresponding to the preceding CSI frame that is closest to the missing CSI frame, as shown in Equation 1. In another embodiment, the missing CSI estimate can be approximated as equivalent to a succeeding available CSI estimate $\widetilde{\mathcal{H}}_{q_2,k}$ corresponding to the succeeding CSI frame that is closest to the missing CSI frame, as shown in Equation 2. More generally, the missing CSI frame can be approximated as some function of multiple available CSI estimates including the preceding and the succeeding available CSI frames, as shown in Equation 3. For example, the function can be an interpolation of at least one of an amplitude or a phase. For example, the function can be a linear interpolation based on the two available CSI estimates $\widetilde{\mathcal{H}}_{q_1,k}$ and $\widetilde{\mathcal{H}}_{q_2,k}$.

$$\widetilde{\mathcal{H}}_{p,k} = \widetilde{\mathcal{H}}_{q_1,k} \tag{1}$$

$$\widetilde{\mathcal{H}}_{p,k} = \widetilde{\mathcal{H}}_{q_2,k} \tag{2}$$

$$\widetilde{\mathcal{H}}_{p,k} = f(\widetilde{\mathcal{H}}_{q_1,k}, \widetilde{\mathcal{H}}_{q_2,k}) \tag{3}$$

As an example scenario, if Frame 49 and Frame 52 are successfully received, but the missing CSI frames are Frame 50 and Frame 51, then the STA 311 has an available CSI estimate corresponding to each of Frame 49 and Frame 52, but the STA 311 does not have data available from the Frame 50 and Frame 51 to execute channel estimation. To approximate the missing CSI estimates corresponding to the missing Frames 49 and 50, the STA 311 can compute $\widetilde{\mathcal{H}}_{50,k}=$ f($\widetilde{\mathcal{H}}_{49,k}$, $\widetilde{\mathcal{H}}_{52,k}$) as first function and $\widetilde{\mathcal{H}}_{51,k}=$ f($\widetilde{\mathcal{H}}_{49,k}$, $\widetilde{\mathcal{H}}_{52,k}$) as a second function that is the same as or different from the first function, respectively.

At block 530, the compensation for the AGC gain error, timing offset error, and phase offset error for the CSI are performed to obtain the cleaned CSI. At block 540, outliers in the cleaned CSI are identified, removed, and interpolated. At block 550, the cleaned CSI can be used to further determine if a breathing rate estimation is required. If the determination at block 550 is a no, then the method 500 ends. If the determination at block 550 is a yes, then the method 500 proceeds to block 560. At block 560, the different spatial components of the cleaned CSI are identified, and their and their Doppler-delay or Doppler-frequency response are obtained. At block 570, based on the cleaned CSI, which of the multiple proposed algorithms to use for breathing rate estimation is determined. At block 580, the determined algorithm for breathing rate estimation is run to generate the breathing estimate. Finally, at block 590, additional steps may be run on the breathing estimate, such as feeding to a tracking algorithm, using as prior information for next iterations of the estimation, determining if the breathing estimation process needs to be terminated etc.

Figure 6:
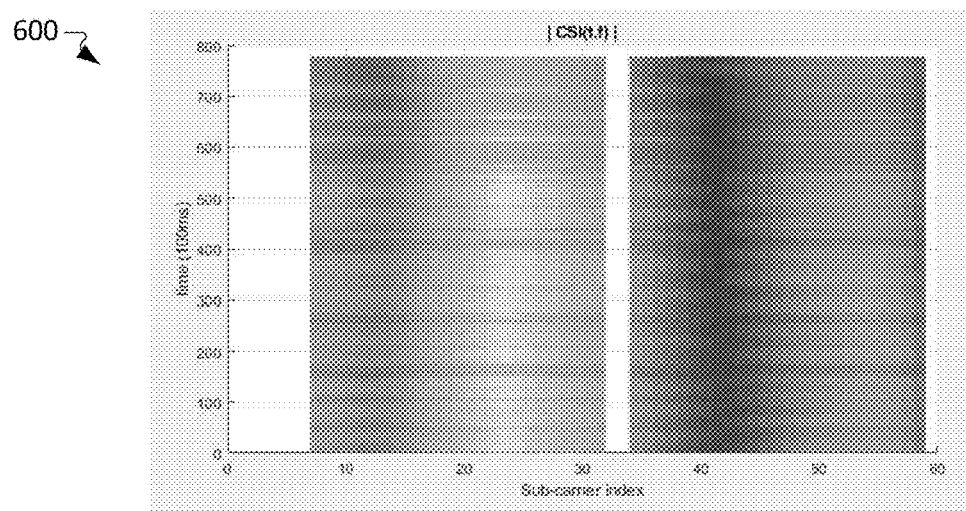
FIG. 6 illustrates an example CSI amplitude that has discrete jumps over time due to automatic gain control (AGC) gain, in accordance with an embodiment of this disclosure.
Figure 7:
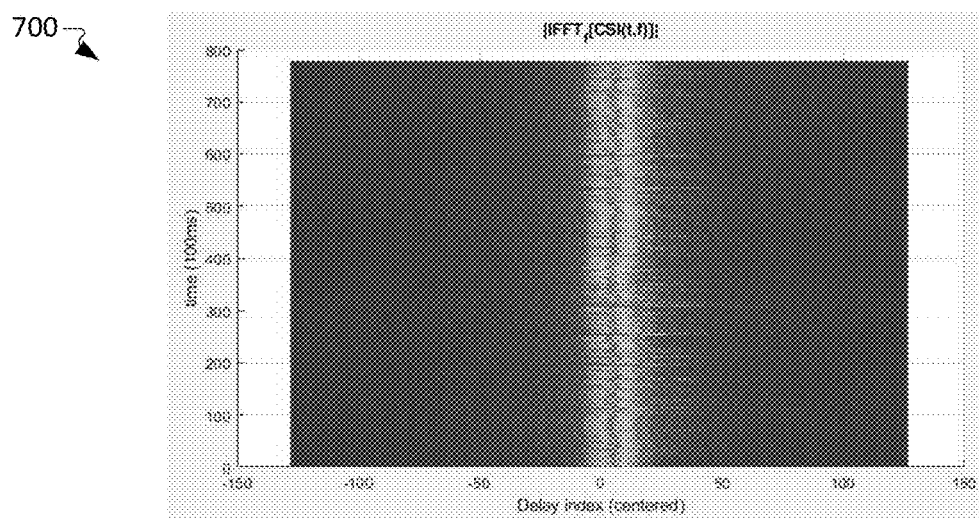
FIG. 7 illustrates an example channel impulse response (CIR) amplitude that has random jitter over time due to symbol start error, in accordance with an embodiment of this disclosure.

FIGS. 6 and 7 illustrate graphs 600 and 700 plotting an unprocessed CSI, as received at the STA 311 as function of time, wherein the frame index p represents time. Due to the synchronization errors and hardware impairments of the STA 311, the obtained noisy CSI can be modelled as an impairment model shown in Equation 4.

$$\widetilde{\mathcal{H}}_p = g_p \odot \mathcal{H}_{p,k} e^{j(2\pi f_k \Delta \tau_p + \psi_p)} \quad (4)$$

In this impairment model, $\widetilde{\mathcal{H}}_p$ denotes the uncompensated (e.g., including the impact of impairments; raw; unprocessed) CSI estimated from the p-th CSI frame. This uncompensated CSI $\widetilde{\mathcal{H}}_p$ can be represented mathematically in the form of a channel matrix. The term $\mathcal{H}_{p,k}$ denotes the true (i.e., without impact of impairments) MN×1 CSI on the k-th sub-carrier of the p-th CSI frame between the TX and the RX. The term HPK can be expressed according to Equation 5, where the term $\mathcal{B}_k$ denotes the static component of the CSI; and the term $D_{p,k}$ denotes the dynamic component of the CSI.

$$\mathcal{H}_{p,k} = \mathcal{B}_k + D_{p,k} \quad (5)$$

The term $g_p$ is an MN×1 real vector representing the gain from the automatic gain control circuit at the receiver 311. The operator $\odot$ denotes the element-wise product of two vectors (also called Hadamard product). The term $\Delta \tau_p$ denotes the timing synchronization offset at the receiver 311 for the p-th CSI frame p. The term $f_k$ denotes the frequency-offset of the k-th subcarrier from the carrier frequency. The term $\psi_p$ denotes the carrier phase-offset of the receiver 311 for CSI frame p. In some embodiments, for correcting the errors the impairment model is based on an assumption that the true CSI is quasi-static over time, as expressed in Equation 6.

$$\mathcal{H}_{0,k} \approx \mathcal{H}_{1,k} \approx \ldots \approx \mathcal{H}_{P-1,k} \text{ for any } k \in \mathcal{K} \quad (6)$$

Particularly, FIG. 6 illustrates a graph 600 of an example CSI amplitude that has discrete jumps over time due to AGC gain, in accordance with an embodiment of this disclosure. The CSI is a function of time and frequency, illustrated as |CSI(t,f)|. The x-axis represents a subcarrier index, for example, in a range from 0 through 60. The y-axis represents time (e.g., in units of 100 milliseconds), for example, in a range of from 0 through 800. The embodiment of the graph 600 of CSI amplitude over time shown in FIG. 6 is for illustration only, and other embodiments could be used without departing from the scope of this disclosure.

FIG. 7 illustrates an example graph 700 of a channel impulse response (CIR) amplitude that has random jitter over time due to symbol start error, in accordance with an embodiment of this disclosure. The CIR is an inverse Fast Fourier transform (IFFT) of the time-dependent frequency-dependent CSI, illustrated as |IFFT$_f$([CSI(t,f)])|. The x-axis represents a delay index (centered), for example, in a range from −150 through 150. The y-axis represents time (e.g., in units of 100 milliseconds), for example, in a range of from 0 through 800. The embodiment of the graph of CIR amplitude 700 over time shown in FIG. 7 is for illustration only, and other embodiments could be used without departing from the scope of this disclosure.

Figure 8:
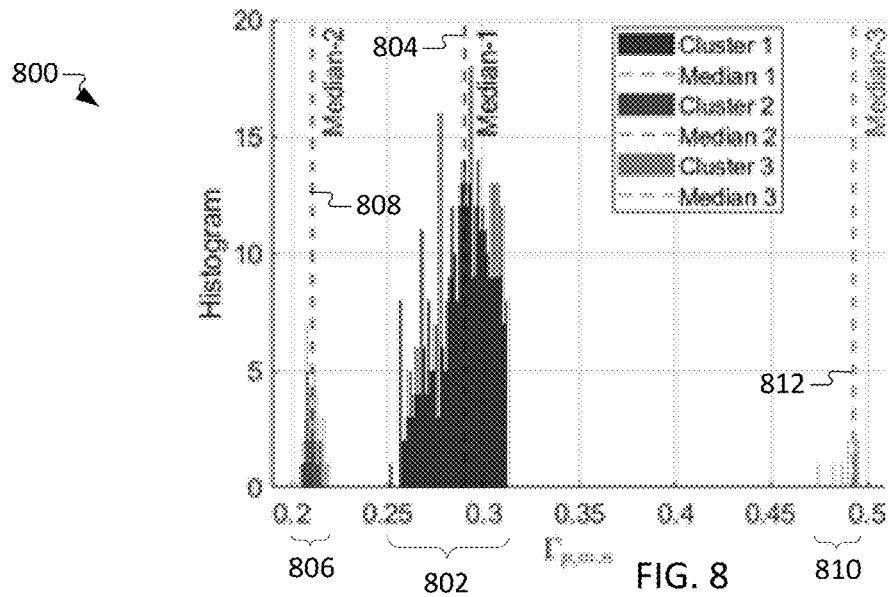
FIG. 8 illustrates an example clustering histogram as part of an AGC gain compensation using density-based spatial clustering of applications with noise ("DB-scan") based clustering algorithm of CSI power for a particular antenna pair for a particular CSI frame, according to embodiments of the present disclosure.

FIG. 8 illustrates an example clustering histogram 800 as part of an AGC gain compensation using density-based spatial clustering of applications with noise ("DB-scan") based clustering algorithm of $\Gamma_{p,m}$, according to embodiments of the present disclosure. The term $\Gamma_{p,m}$ represents CSI power for an m-the antenna pair for a p-th CSI frame. The embodiment of the clustering histogram 800 shown in FIG. 8 is for illustration only, and other embodiments could be used without departing from the scope of this disclosure. To remove or reduce amplitude errors caused by AGC gain at the receiver, and to generate AGC gain-compensated CSI, the clustering histogram 800 shown in FIG. 8 can be generated as part of the compensation procedure performed at block 530 of FIG. 5.

The majority of the surfaces in many environments are stationary surfaces, such as in the indoor environment 370 shown in FIG. 3, where a minority signals transmitted from the AP 301 reflect off a moving surface, such as the subject's 380 torso.

Due to the quasi-static nature of the channel and/or CSI, it can be expected that for any antenna pair m that the CSI power for the true channel, as expressed according to Equation 7, is constant over the period of time $0 \leq p \leq P-1$ during which P CSI frames 402 are transmitted.

$$\Gamma_{p,m} = \sum_{k \in \mathcal{K}} \frac{1}{K} |[\mathcal{H}_{p,k}]_m|^2 \quad (7)$$

Correspondingly, in one embodiment, for each antenna pair $1 \leq m \leq MN$, a clustering algorithm can be executed on the values of CSI power $\{\Gamma_{p,m} | 0 \leq p \leq P-1\}$ to identify the clusters corresponding to different AGC gain values. For the particular antenna pair m, the number of clusters identified is denoted as W, with each cluster indexed by w. Examples of the clustering algorithm include DB-scan clustering or K-means clustering. For each identified cluster, the average value (e.g., median or mean) of a square-root ($\sqrt{\Gamma_{p,m}}$) of each measured CSI power value within the cluster can be used as the estimated AGC gain term $[\hat{g}_p]_m$. For each antenna pair m, the CSI with the AGC gain compensated can then be obtained as expressed in Equation 8:

$$[\overline{\mathcal{H}}_{p,k}]_m = [\tilde{\mathcal{H}}_{p,k}]_m / [\hat{s}_p]_m \quad (8)$$

The clustering histogram 800 shows three clusters (W=3) including a first cluster 802 (Cluster 1) having a first median value 804 (Median-1), a second cluster 806 having a second median value 808, and a third cluster 810 (Cluster 3) having a third median value 812.

In another embodiment, a determination is made whether to compensate for the one or more errors in the amplitude of the respective CSI frame that is indexed by p among P CSI frames. To make this determination, a sequential methodology can be executed, where if $|\Gamma_{p,m}-\Gamma_{p-1,m}| \geq$ Threshold, then we obtain (e.g., generate) the ACG gain-compensated CSI as expressed in Equation 9. That is, this determination is based on whether a difference between CSI power values measured for consecutive CSI frames is exceeded by a threshold value.

$$[\overline{\mathcal{H}}_{p,k}]_m = [\tilde{\mathcal{H}}_{p,k}]_m \sqrt{\frac{\Gamma_{p-1,m}}{\Gamma_{p,m}}} \quad (9)$$

Figure 9:
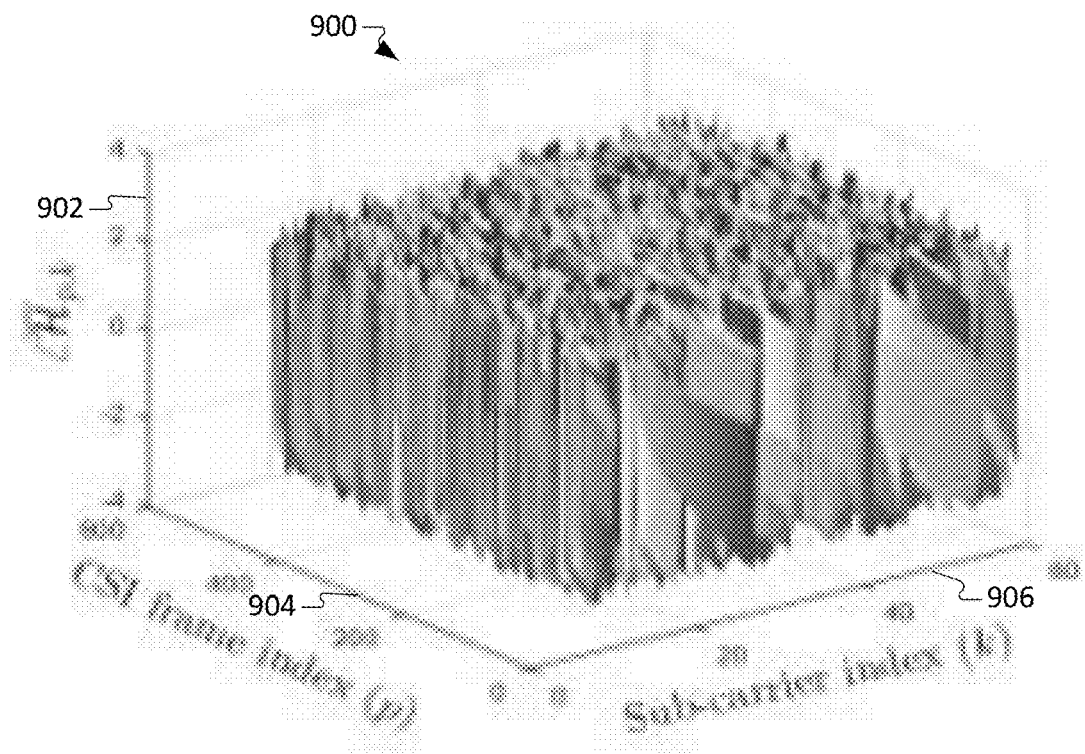
FIG. 9 illustrates an example CSI phase before compensation for the timing and phase errors, according to embodiments of the present disclosure.
Figure 10:
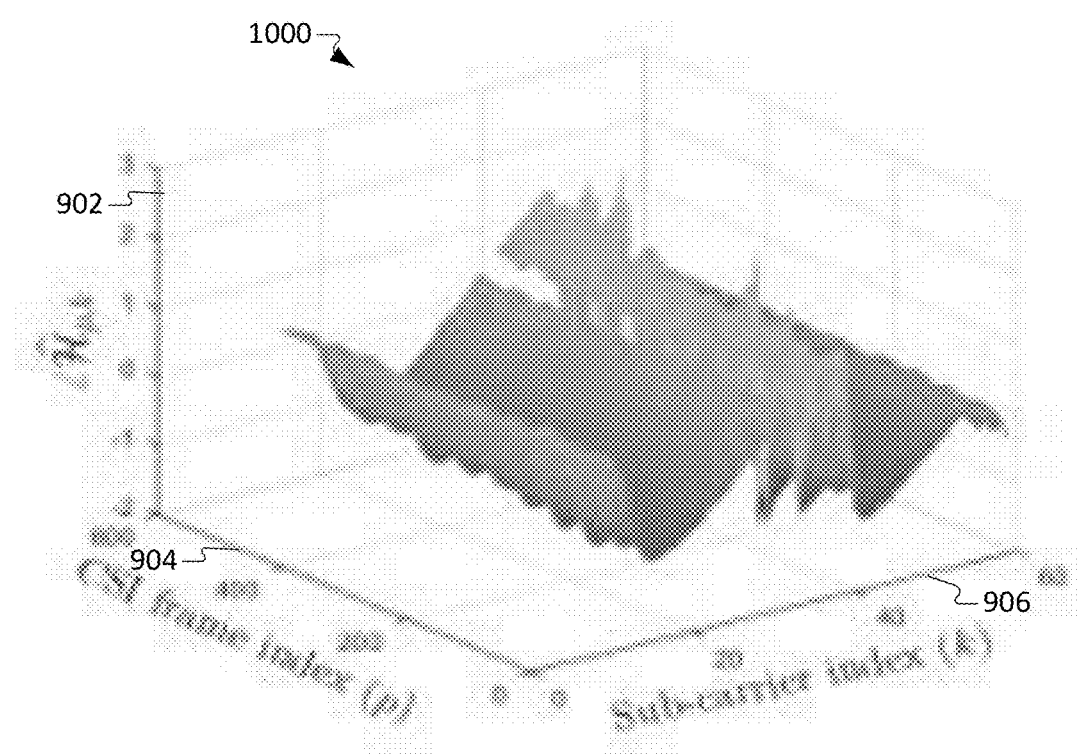
FIG. 10 illustrates an example CSI phase after compensation for the timing and phase errors of FIG. 9.

FIG. 9 illustrates an example CSI phase 900 before compensation for the timing and phase errors, according to embodiments of the present disclosure. FIG. 10 illustrates the example CSI phase 1000 of FIG. 9 after compensation for the timing and phase errors. In FIGS. 9 and 10, the CSI phase is an AGC gain-compensated CSI, including an angular dimension 902 labeled as "$\angle \overline{\mathcal{H}}_{p,k}$", a time dimension 904 labeled as "CSI frame index (p)", and a frequency dimension 906 labeled as "Sub-carrier index (k)."

Due to the quasi-static nature of the channel and/or CSI, it can be expected that the true CSI is approximately equivalent to the static component of the CSI (i.e., $\mathcal{H}_{p,k} \approx \mathcal{B}_k$) over the period of time $0 \leq p \leq P-1$ during which P CSI frames 402 are transmitted. Correspondingly in one embodiment, for a given $\mathcal{B}_k$ as the static component of the CSI, the timing error $\Delta\tau_p$ and phase-error $\psi_p$ for any CSI frame p can be computed as expressed in Equations 10 and 11, respectively. The term T denotes a search range for the value of $\widehat{\Delta\tau_p}$. The term $\hat{\mathcal{B}}_k$ denotes an estimate of the static component $\mathcal{B}_k$ of the CSI. This method may utilize an apriori estimate $\hat{\mathcal{B}}_k$ of $\mathcal{B}_k$.

$$\widehat{\Delta\tau_p} = \arg\max_{\tau \in T} \left| e^{j2\pi f_k \tau} \overline{\mathcal{H}}_{p,k}^\dagger \hat{\mathcal{B}}_k \right| \quad (10)$$

$$\widehat{\psi_p} = \text{angle}\left\{ \sum_{k \in \mathcal{K}} e^{j2\pi f_k \widehat{\Delta\tau_p}} \overline{\mathcal{H}}_{p,k}^\dagger \hat{\mathcal{B}}_k \right\} \quad (11)$$

In another embodiment, for given estimate of the static component $\hat{\mathcal{B}}_k$, the timing error $\Delta\tau_p$ and phase-error $\psi_p$ for any CSI frame p can be computed as solution of the weighted least-squares problem shown in Equation 12. This embodiment may utilize an apriori estimate $\hat{\mathcal{B}}_k$ of $\mathcal{B}_k$.

$$\widehat{\Delta\tau_p}, \widehat{\psi_p} = \arg\min_{\tau, \psi} \left\{ \sum_{k \in \mathcal{K}} \|\hat{\mathcal{B}}_k\|^2 \left(2\pi f_k \tau - \psi + \mathcal{U}\left[\text{angle}\left\{\overline{\mathcal{H}}_{p,k}^\dagger \hat{\mathcal{B}}_k\right\}\right]\right)^2 \right\} \quad (12)$$

The function $\mathcal{U}[.]$ is a phase unwrapping function that ensures that the phase-difference for adjacent sub-carriers is less than π, as shown in Equation 13:

$$|\mathcal{U}[\text{angle}\{\overline{\mathcal{H}}_{p,k}^\dagger \hat{\mathcal{B}}_k\}] - \mathcal{U}[\text{angle}\{\overline{\mathcal{H}}_{p,k-1}^\dagger \hat{\mathcal{B}}_{k-1}\}]| \leq \pi \quad (13)$$

Correspondingly the CSI after phase and timing error compensation is referred to as the compensated ("cleaned") CSI can be obtained as expressed in Equation 14:

$$\widehat{\mathcal{H}}_{p,k} = \overline{\mathcal{H}}_{p,k} e^{-j(2\pi f_k \widehat{\Delta\tau_p} + \widehat{\psi_p})} \quad (14)$$

In some embodiments, the estimate $\hat{\mathcal{B}}_k$ of the static component of CSI can be expressed as a MN×1 all-one vector: $\mathbb{1}_{MN}$. In another embodiment, the estimate $\hat{\mathcal{B}}_k$ of the static component of CSI can be expressed according to Equation 15.

$$\hat{\mathcal{B}}_k = \sum_{k \in \mathcal{K}} |\overline{\mathcal{H}}_{p,k}|/K \quad (15)$$

In yet another embodiment, the estimate $\hat{\mathcal{B}}_k$ of the static component of CSI can be expressed according to Equation 16, namely, the estimate $\hat{\mathcal{B}}_k$ of the static component from the previous estimation round.

$$\hat{\mathcal{B}}_k = \sum_{q=-P}^{-1} \widehat{\mathcal{H}}_{q,k}/P \quad (16)$$

In yet another embodiment, the estimation of $\widehat{\Delta\tau_p}$, $\widehat{\psi_p}$ may be performed chronologically from the CSI frame p=0 to CSI frame p=P-1. To estimate $\widehat{\Delta\tau_p}$, $\widehat{\psi_p}$ for any p, the value of $\hat{\mathcal{B}}_k$ to use can be obtained as expressed in Equation 17:

$$\hat{\mathcal{B}}_k = \sum_{q=0}^{p-1} \widehat{\mathcal{H}}_{q,k}/p \quad (17)$$

In some embodiments, after obtaining the compensated ("cleaned") CSI $\widehat{\mathcal{H}}_{p,k}$ for all the p sequentially, the estimate $\hat{\mathcal{B}}_k$ of the static component is fixed as expressed in Equation 18, and a second iteration of re-estimating $\widehat{\Delta\tau_p}$, $\widehat{\psi_p}$ for all p=1, . . . , P-1 with this updated value of $\hat{\mathcal{B}}_k$ is executed.

$$\hat{\mathcal{B}}_k = \sum_{p=0}^{P-1} \widehat{\mathcal{H}}_{p,k}/P \quad (18)$$

The above-described procedure of compensating the CSI for the timing and phase errors involves a joint timing and phase correction method, where all the MN antenna dimensions are jointly compensated ("cleaned") of the CSI timing and phase-errors. In another embodiment, the same process of compensating the CSI for the timing and phase errors can be used but the timing and phase errors can be estimated and corrected independently for each antenna dimension.

Outlier Detection and Removal

Some CSI samples (e.g., compensated CSI estimate) $\widehat{\mathcal{H}}_{p,k}$ may still be too corrupted after completing the following three compensations: (1) approximating missing CSI estimates; (2) AGC gain error compensation; (3) Phase error and timing error compensation(s). Using such CSI samples can degrade breathing rate performance. The fact that CSI is quasi-static can be used to identify such CSI samples that are still too corrupted. For example, in one embodiment, after completing the above-listed three compensations, the metric expressed in Equation 19 can be utilized as an identifier of the corrupted CSI samples. A corrupted CSI frame p is identified based on a determination that the comparison in Equation 19 is TRUE.

$\sum_{k \in \mathcal{K}} | \widehat{\mathcal{H}}_{p,k} - \overline{\mathcal{B}}_k |^2 \geq \text{Outlier}_{threshold} \times (\sum_{k \in \mathcal{K}} \|\overline{\mathcal{B}}_k\|^2)$, where $\overline{\mathcal{B}}_k = \sum_{p=0}^{P-1} \widehat{\mathcal{H}}_{p,k}/P$. (19)

Such a corrupted CSI frame p can be replaced by the previous CSI frame, as expressed in Equation 20. In another embodiment, an interpolation of the previous and succeeding CSI frames can also be used to replace the corrupted CSI frame, which is a similar procedure as block 520.

$$\widehat{\mathcal{H}}_{p,k} = \widehat{\mathcal{H}}_{p-1,k}. \qquad (20)$$

In certain embodiments, a corrupted CSI estimate is detected based on a comparison of the magnitude of the gain-compensated CSI estimate $|\widehat{\mathcal{H}}_{p,k}|$ to the mean of magnitude of the P gain-compensated CSI estimates expressed as $\overline{\mathcal{B}}_k = \sum_{p \in \mathcal{P}} |\widehat{\mathcal{H}}_{p,k}|/P$. The comparison includes determining whether a sum (across sub-carriers k) of the squared error between $|\widehat{\mathcal{H}}_{p,k}|$ and $\overline{\mathcal{B}}_k$ is greater than an outlier threshold. In such embodiments, the receiver can be configured to: identify a magnitude of an AGC gain-compensated CSI estimate ($|\widehat{\mathcal{H}}_{p,k}|$) corresponding to each of the P CSI estimates; identify a mean of magnitude of the P AGC gain-compensated CSI estimates expressed as $\overline{\mathcal{B}}_k = \sum_{p \in \mathcal{P}} |\widehat{\mathcal{H}}_{p,k}|/P$; detect a corrupted CSI estimate based on a determination that a comparison is TRUE, wherein the comparison includes determining whether, for each of K sub-carriers indexed by k, a sum of a squared error between the $|\widehat{\mathcal{H}}_{p,k}|$ and the $\overline{\mathcal{B}}_k$ is greater than an outlier threshold; and replace the corrupted CSI frame within the P compensated CSI estimates.

Figure 11A:
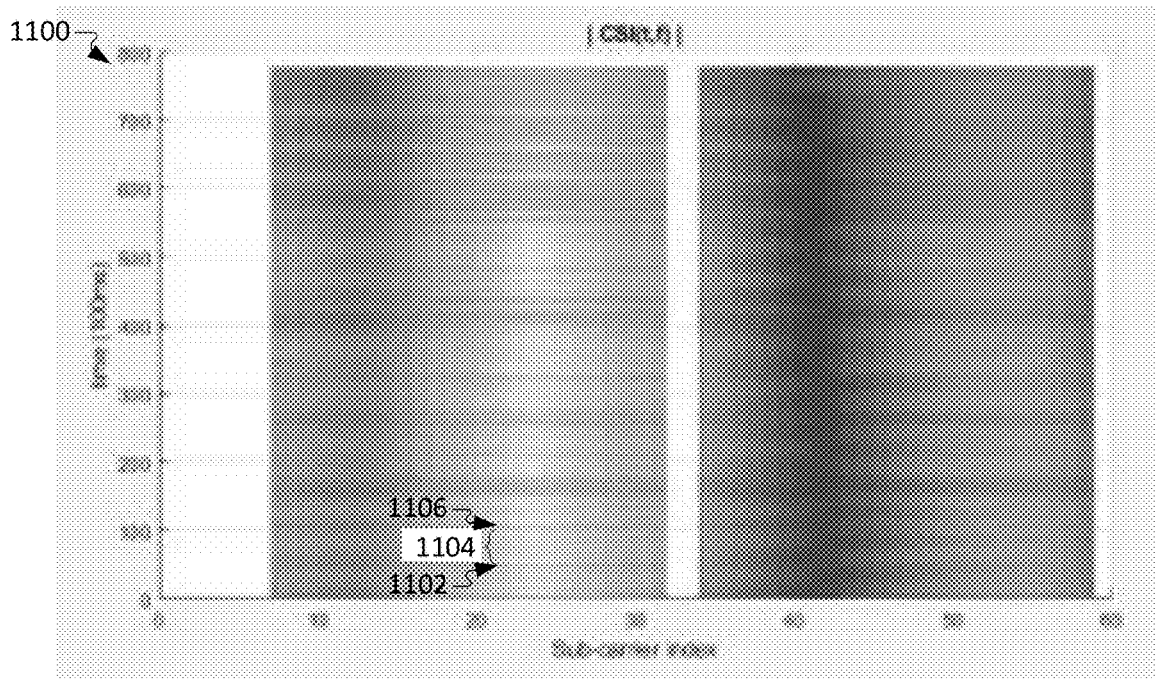
FIGS. 11A and 11B illustrate an example CSI magnitude before and after compensating for impairments, respectively, according to embodiments of this disclosure.
Figure 11B:
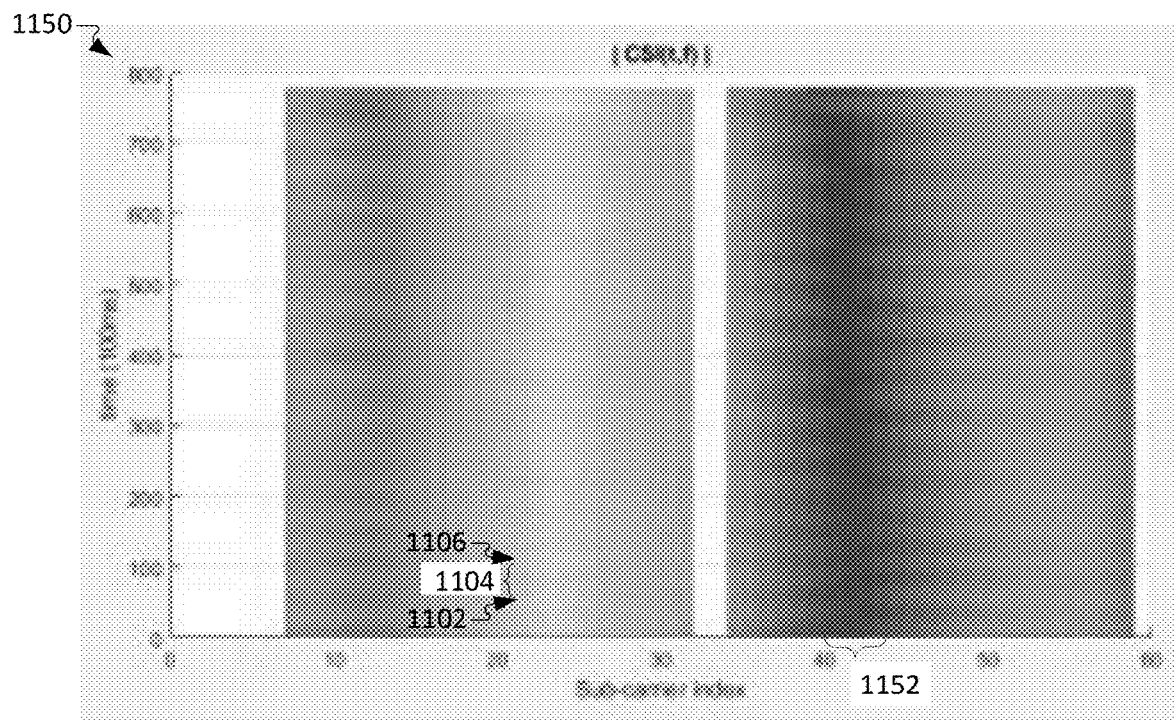

FIGS. 11A and 11B illustrate an example CSI magnitude ($|\widehat{\mathcal{H}}_{p,k}|$) 1100 and 1150 before and after compensating for impairments, respectively, according to embodiments of this disclosure. These impairments include at least one of: a missing CSI estimate, AGC gain error or other error in CSI amplitude, a timing error $\Delta\tau_p$ or a phase-error $\psi_p$ for any CSI frame p. The uncompensated CSI magnitude 1100 exhibits abrupt variations of magnitude over time caused by different AGC gain levels, which is similar to the abrupt variations of magnitude within a single subcarrier index shown in FIG. 6. As an example of abrupt variations within a same subcarrier index, the CSI magnitude 1100 switches from a first AGC gain level 1102 to a second AGC gain level 1104 at a first time, and then the magnitude switches to a third AGC gain level 1106 at a second time. The first and third AGC gain levels 1102 and 1106 can be the same or approximately equivalent to each other, but both 1102 and 1106 are obviously varied from the second AGC gain level 1104. FIG. 11B shows that that the CSI magnitude 1150 as a function of time and carrier index exhibits a smooth pattern over time.

Figure 12A:
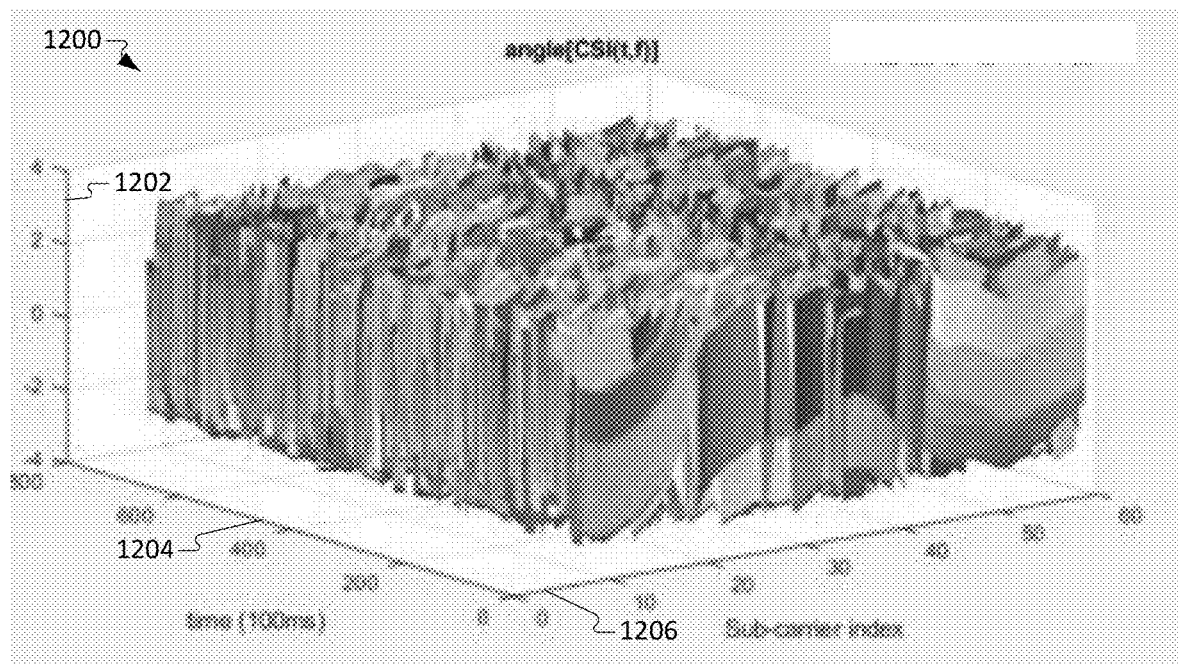
FIGS. 12A and 12B illustrate an example CSI phase before and after compensating for impairments, respectively, according to embodiments of this disclosure.
Figure 12B:
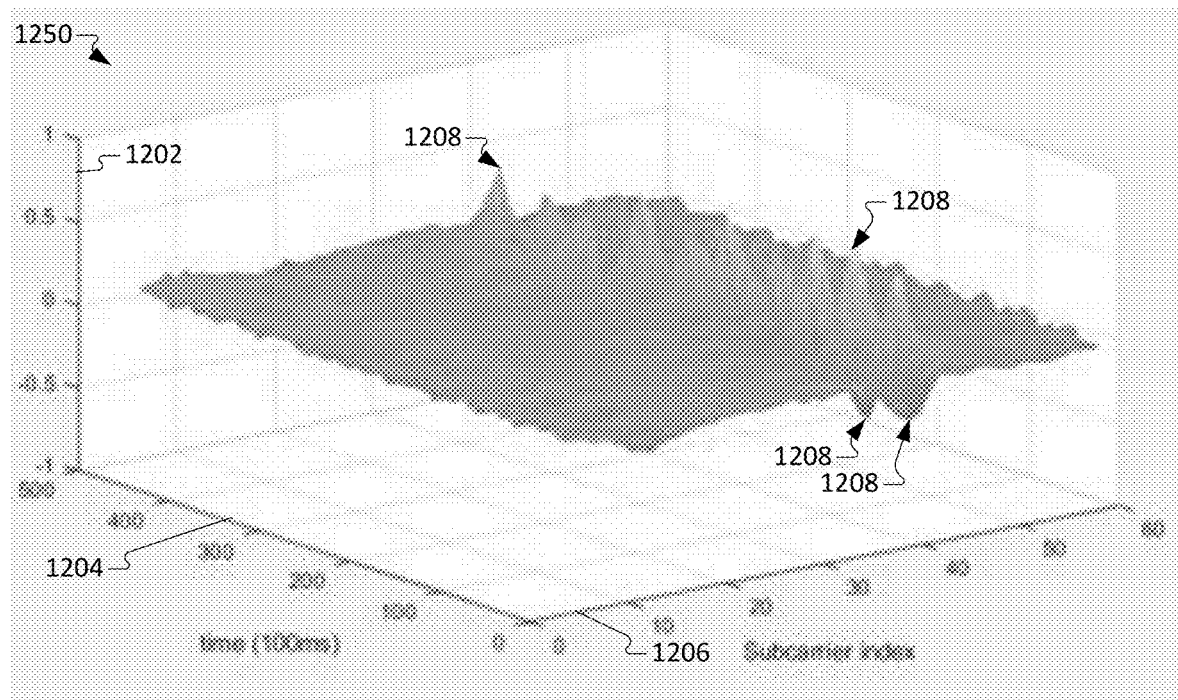

FIGS. 12A and 12B illustrate an example CSI phase ($\angle \widehat{\mathcal{H}}_{p,k}$) 1200 and 1250 before and after compensating for impairments, respectively, according to embodiments of this disclosure. The three dimensions of phase angle 1202, time 1204 in units of 100 milliseconds (ms), and frequency 1206 shown in FIGS. 12A and 12B are the same as or similar to the three corresponding dimensions 902, 904, and 906 of FIGS. 9 and 10. In FIG. 12B, the values of the CSI phase 1250 are nearly all zero or very close to zero, except for a few spikes 1208 that can be ignored as having negligible amplitude (1152 of FIG. 11B). When the amplitude is too small, then the spikes result from a small amount of noise.

Figure 13A:
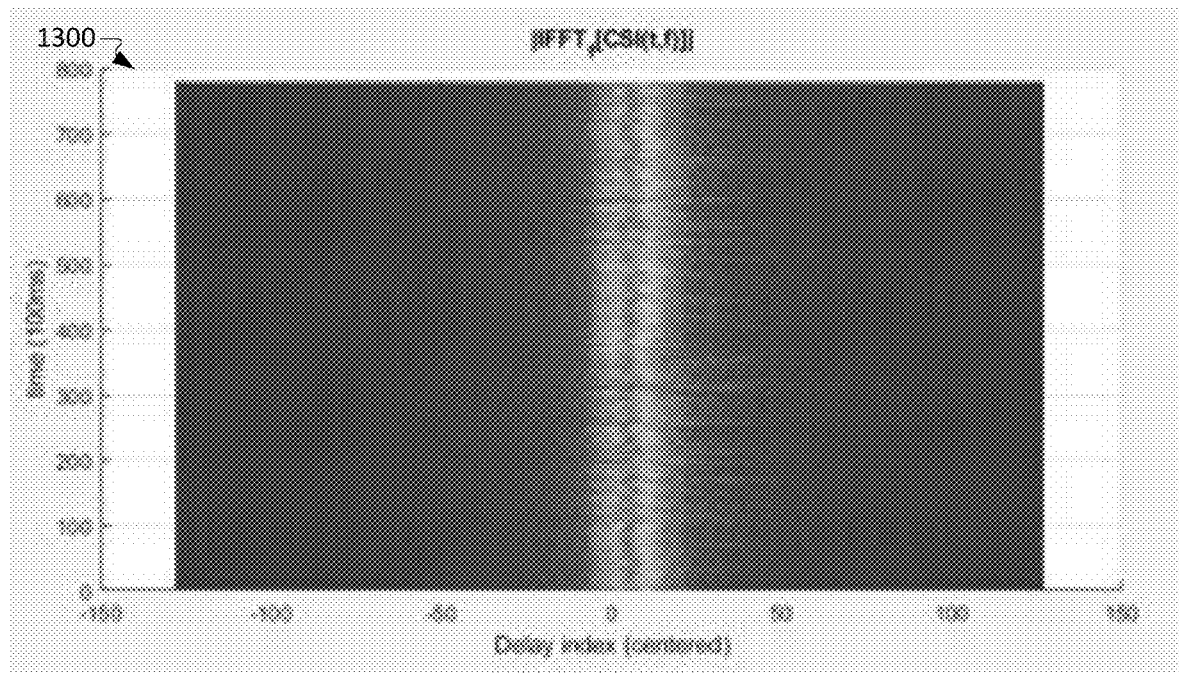
FIGS. 13A and 13B illustrate an example CIR magnitude that is a Fourier transform of the CSI magnitude of FIGS. 11A and 11B.
Figure 13B:
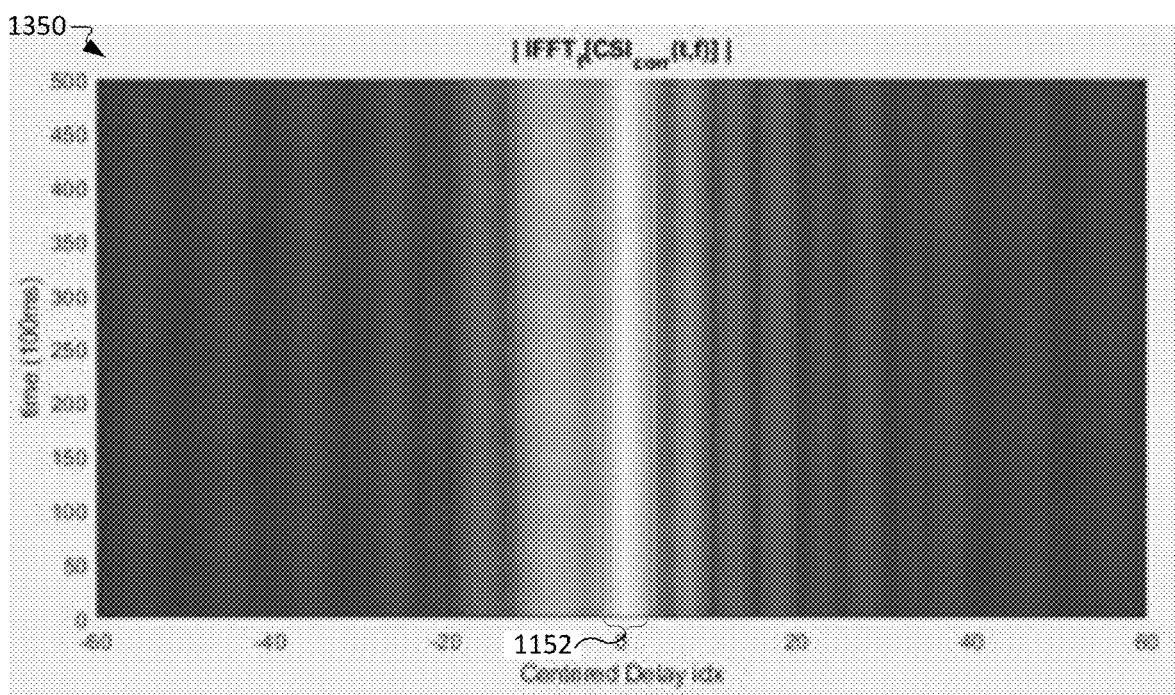

FIGS. 13A and 13B illustrate an example channel impulse response (CIR) magnitude ($|\tilde{H}_p(u)|$) 1300 and 1350 that is a Fourier transform of the CSI magnitude ($|\widehat{\mathcal{H}}_{p,k}|$) of FIGS. 11A and 11B. The time-random jitter shown in the CIR magnitude 1300 before compensating for impairments is similar to the jitter shown in the CIR amplitude graph 700 of FIG. 7. However, such jitter is removed, as shown by the clean pattern of a stable CIR magnitude 1350 in FIG. 13B.

Sometimes the compensated CSI estimate $\widehat{\mathcal{H}}_{p,k}$ is in an ideal condition after completing the following three compensations: (1) approximating missing CSI estimates; (2) AGC gain error compensation; (3) Phase error and timing error compensation(s). FIG. 14 illustrates an example compensated CSI ($\widehat{\mathcal{H}}_{p,k}$) 1400 in the ideal condition in which there are no residual errors and no corrupted samples are identified, according to embodiments of this disclosure. That is, the compensated CSI 1400 has a sinusoidal variation with the breathing signal of the subject 380. The ideal compensated CSI 1400 can be based on the assumption that all hardware and synchronization impairments are removed by the three above-listed compensations, and can be expressed according to Equation 21. Using Taylor expansion, the ideal compensated CSI 1400 can be expressed according to Equation 22.

$$\widehat{\mathcal{H}}_{p,k} = \overline{\mathcal{B}}_k + \alpha_0 a_0 e^{-j2\pi f_c \tau_0} \sin(2\pi f_{br} p T_{rep} + \phi) e^{-j2\pi f_k \tau_0} + \text{noise} \qquad (21)$$

$$\widehat{\mathcal{H}}_{p,k} \approx -j2\pi f_c \tau_0 \alpha_0 a_0 \sin(2\pi f_{br} p T_{rep} + \phi) e^{-j2\pi f_k \tau_0} + \text{constant} + \text{noise} \qquad (22)$$

The breathing signal of the subject 380 is distributed across all subcarriers k and time samples p, and power of the MPC We can be focused upon and isolated by converting from (time,freq)-domain to (Doppler-delay)-domain. More particularly, the ideal compensated CSI 1400 is based on an assumption that the dynamic component includes the breathing rate of the subject 380, and the sinusoidal breathing signal can be expressed according to Equation 23.

$$\sin(2\pi f_{br} p T_{rep} + \phi) \qquad (23)$$

FIG. 15 illustrates an Inverse Fast Fourier Transform (IFFT$_k$) 1500 of the compensated CSI of FIG. 14, according to embodiments of this disclosure. In FIG. 15, the IFFT$_k$ 1500 includes a first dimension 1502 labeled as "|IFFT$_f$[CSI$_{compensated}$(t, f)]|", a time dimension 1504 in units of 100 ms, and a third dimension 1506 labeled as "centered delay index."

FIG. 16 illustrates an example Doppler spectrum 1600 as a Fourier Transform (FFT$_p$) over the time domain of the compensated CSI of FIG. 15 containing peaks 1602 corresponding to the frequency of breathing (i.e., breathing rate) $f_{br}$ of the subject 380, according to embodiments of this disclosure. The Doppler spectrum 1600 includes a first dimension 1604 labeled as "|FFT$_t$(IFFT$_f$(CSI$_{compensated}$(t, f)))|", a Doppler dimension 1606 in units of Hertz, and a third dimension 1608 labeled as "centered delay index."

Figure 17A:
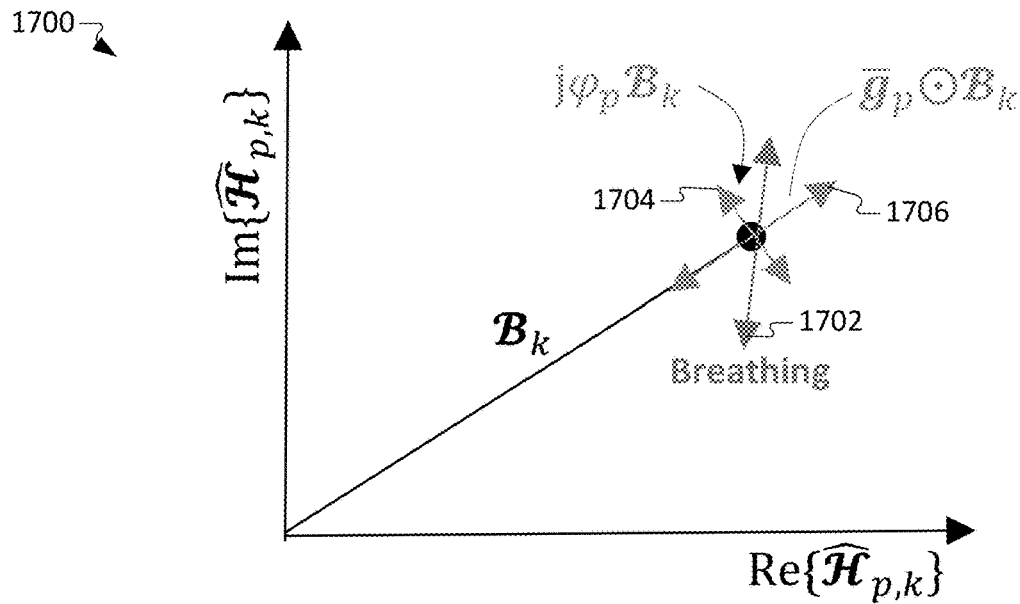
FIGS. 17A and 17B illustrate real and imaginary components of a compensated CSI and before and after rotating the compensated CSI, respectively, to demonstrate an impact of residual impairments, according to embodiments of this disclosure.
Figure 17B:
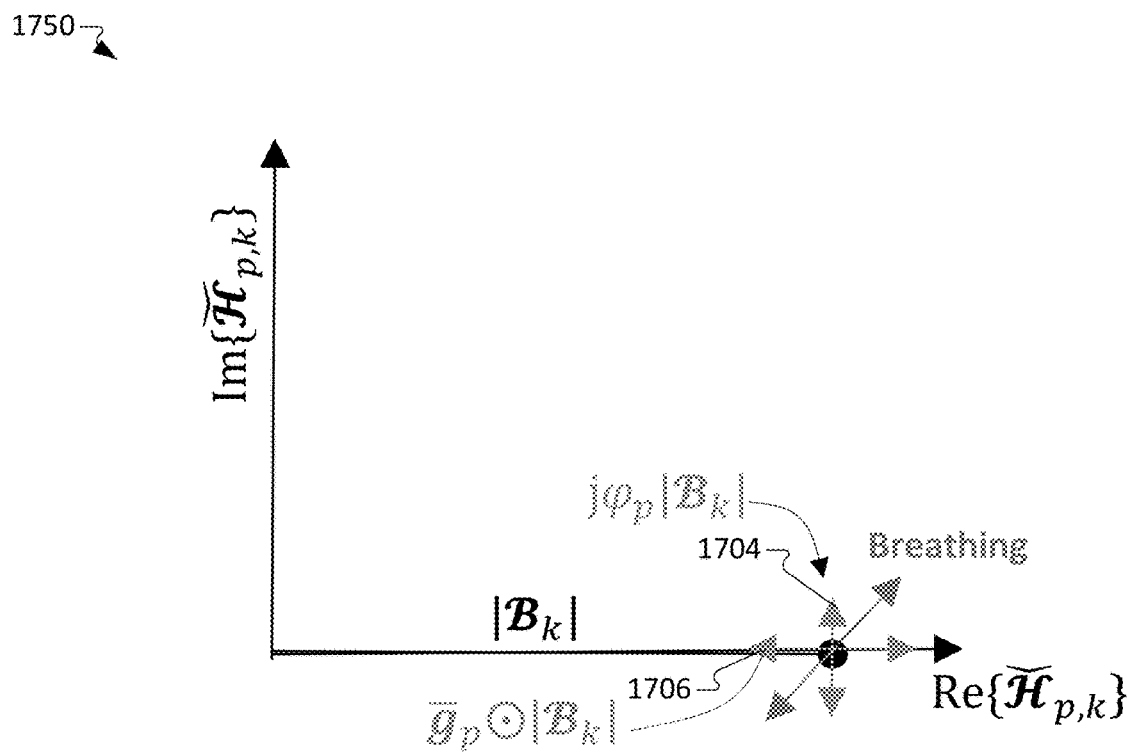

To demonstrate an impact of residual impairments, FIGS. 17A and 17B illustrate real and imaginary components of a compensated CSI 1700 and 1750 before and after rotating the compensated CSI, respectively, according to embodiments of this disclosure.

Small residual impairments can still remain in some CSI samples (e.g., compensated CSI estimate) $\widehat{\mathcal{H}}_{p,k}$ even after completing the following three compensations: (1) approximating missing CSI estimates; (2) AGC gain error compensation; (3) phase error and timing error compensation(s). On example of these small residual impairments is a MN×1 residual AGC gain error denoted as $\bar{g}_p$. Another example of these small residual impairments is a residual phase-error $\varphi_p$ for CSI frame p. The compensated CSI $\widetilde{\mathcal{H}}_{p,k}$ can be modeled according to Equation 24, based on an assumption that the static component $\mathcal{B}_k$ of the CSI does not vary with the breathing of the subject 380.

$$\widetilde{\mathcal{H}}_{p,k} = (1_{MN\times1} + \bar{g}_p) \odot \mathcal{H}_{p,k} e^{-j\varphi_p} \approx \mathcal{B}_k + \bar{g}_p \odot \mathcal{B}_k - j\varphi_p$$
$$\mathcal{B}_k + \alpha_0 a_0 e^{-j2\pi f_c \bar{\tau}_0 \sin(2\pi f_{br} p T_{rep} + \phi)} e^{-j2\pi f_k \tau_0} \quad (24)$$

Rotating the compensated CSI estimate $\widetilde{\mathcal{H}}_{p,k}$, in the case of multiple Tx antenna and multiple Rx antennas, ensures that the small residual impairments $\bar{g}_p$ and $\varphi_p$ are only present along some of the dimension, not all of the dimensions. In an example scenario, the CSI is distributed across in a four dimensional space defined by four antenna pairs corresponding to 2 Tx antennas and 2 Rx antennas, but all of the noise lies along only one axis or two of the axes. That is, the residual errors are concentrated along those one or two axes. Embodiments of this disclosure ignore those dimensions or directions along which there is a lot of residual error, and focus on (e.g., continue to process) those dimensions where the error is less, thereby enabling the receiver 311 to compute a very clean, compensated estimation of CSI. FIGS. 17A and 17B demonstrate this technical advantage. FIG. 17A shows non-zero real and imaginary values for the subject's breathing signal 1702, and for the residual phase error $\varphi_p$ 1704 and the residual gain error 1706 of the static component $\mathcal{B}_k$. However, as a result of rotating the CSI, FIG. 17B shows non-zero real and imaginary values for the subject's breathing signal 1702, a constant value for the real component of the residual phase error $\varphi_p$ 1704 of the static component $\mathcal{B}_k$, and zero values for the imaginary component of the residual gain error 1756 of the static component $\mathcal{B}_k$.

Estimation of Breathing Rate

Without loss of generality, the MN×1 "true" CSI (i.e., without impact of impairments) on the k-th sub-carrier of the p-th CSI frame between the TX and the RX can be represented according to Equation 25. The channel has L MPCs. Each MPC includes a time-varying amplitude $\alpha_l(p)$, and MN×1 array response vector $a_l(p)$, and a delay $\tau_l(p)$. The term $f_k$ denotes the frequency offset of the k-th subcarrier from the carrier frequency, and the term $f_c$ denotes the carrier frequency.

$$\mathcal{H}_{p,k} = \Sigma_{l=1}^L \alpha_l(p) a_l(p) e^{-j2\pi(f_c + f_k)\tau_l(p)} \quad (25)$$

Furthermore, without loss of generality, it can be assumed that MPC 0 represents the signal path from the AP 301 to the STA 311, that is reflected from the subject's 308 torso. For this MPC 0, due to the movement of the subject's torso, a model of the temporal variation in the MPC amplitude can be expressed as: $\alpha_0(p) = \alpha_0$, and the array response can be expressed as: $a_0(p) = a_0$. The MPC delay can be expressed according to Equation 26, where $\tau_0$ denotes the mean path delay, $\bar{\tau}_0$ denotes the additional delay due to torso movement, and $\phi$ denotes a parameter representing the breathing phase of the subject 380.

$$\tau_0(p) = \tau_0 + \bar{\tau}_0 \sin(2\pi f_{br} p T_{rep} + \phi) \quad (26)$$

Implicitly, the MPC amplitude and array response are assumed to be unaffected by the subject's 380 breathing while the delay is assumed to have a periodic sinusoidal variation, whose frequency is the breathing rate $f_{br}$. Based on an assumption that the static component $\mathcal{B}_k$ of the CSI does not vary with the breathing, the compensated $\widetilde{\mathcal{H}}_{p,k}$ can be modeled as shown in Equation 27, where $\bar{g}_p$ denotes a MN×1 residual AGC gain error after completing AGC gain compensation, and $\varphi_p$ denotes a residual phase-error for CSI frame p after completing phase error and timing error compensation(s).

$$\widetilde{\mathcal{H}}_{p,k} = \mathcal{B}_k + \bar{g}_p \odot \mathcal{B}_k - j\varphi_p \mathcal{B}_k + \alpha_0 a_0 e^{-j2\pi f_c \bar{\tau}_0 \sin(2\pi f_{br} p T_{rep} + \phi)} e^{-j2\pi f_k \tau_0} \quad (27)$$

By multiplying with the phase-angle estimate of the static component $\widehat{\mathcal{B}}_k$, the compensated CSI can further be expressed according to Equation 28:

$$\widehat{\mathcal{H}}_{p,k} = \widetilde{\mathcal{H}}_{p,k} \odot e^{-j\angle \widehat{\mathcal{B}}_k} \approx |\mathcal{B}_k| + \bar{g}_p \odot |\mathcal{B}_k| - j\varphi_p|$$
$$\mathcal{B}_k| + \alpha_0 (a_0 \odot e^{-j\angle \widehat{\mathcal{B}}_k})$$
$$e^{-j2\pi f_c \bar{\tau}_0 \sin(2\pi f_{br} p T_{rep} + \phi)} e^{-j2\pi f_k \tau_0} \quad (28)$$

In one embodiment, the Fourier transform along the p-dimension and inverse-Fourier transform along k-dimension can be taken to obtain the Doppler-delay CSI as shown in Equation 29 and as shown in FIGS. 14-16. The term v denotes the Doppler frequency bin index, and u denotes the delay bin index.

$$\hat{h}(v, u) = \sum_{p=0}^{P-1} \sum_{k \in \mathcal{K}} \frac{\widehat{\mathcal{H}}_{p,k} e^{-\frac{j2\pi v p}{P}} e^{\frac{j2\pi k u}{K}}}{P} \quad (29)$$

Using this Doppler-delay CSI $\hat{h}(v, u)$ of Equation 29 (above), the breathing rate can be estimated using one or more different algorithms. For convenience, the following definitions are provided in Equations 30 and 31:

$$\hat{h}^{(1)}(v, u) = \frac{\hat{h}(v, u) + \hat{h}(-v, u)^*}{2} \quad (30)$$

$$\hat{h}^{(2)}(v, u) = \frac{\hat{h}(v, u) - \hat{h}(-v, u)^*}{2j} \quad (31)$$

Without loss of generality, a set of feasible delay bins $\mathcal{U}_0$ and Doppler bins $\mathcal{V}_0$ that are candidates for the MPC-0 that contains the breathing signal can also be considering. In one embodiment, these feasible bins $\mathcal{U}_0$ and $\mathcal{V}_0$ can be obtained from side information. As an example, the side information can be previous estimates of breathing rate and delay bin obtained.

In the embodiment of Algorithm 1, the estimate of the breathing rate can be obtained as: $\hat{f}_{br} = v_0/(P\ T_{rep})$, where:

$$v_0 = \arg\max_{v \in \mathcal{V}_0} \left\{ \sum_{u \in \mathcal{U}_0} \|\hat{h}(v, u)\|^2 \right\} \quad (32)$$

In the embodiment of Algorithm 2, the estimate of the breathing rate can be obtained as: $\hat{f}_{br} = v_0/(P\ T_{rep})$, where:

$$v_0 = \arg\max_{v \in \mathcal{V}_0} \left\{ \max_{u \in \mathcal{U}_0} \|\hat{h}(v, u)\|^2 \right\} \quad (33)$$

In the embodiment of Algorithm 3, the estimate of the breathing rate can be obtained as: $\hat{f}_{br} = v_0/(P\ T_{rep})$, where:

$$v_0 = \arg\max_{v \in \mathcal{V}_0} \left\{ x_1(v, u) + x_2(v, u) + \sqrt{(x_1(v, u) - x_2(v, u))^2 + 4x_3(v, u)} \right\} \quad (34)$$

$$x_1(v, u) = \left\| \text{Re}\left\{\hat{h}^{(1)}(v, u)\right\} \right\|^2 + \left\| \text{Re}\left\{\hat{h}^{(2)}(v, u)\right\} \right\|^2 \quad (35)$$

$$x_2(v, u) = \left\| \text{Im}\left\{\hat{h}^{(1)}(v, u)\right\} \right\|^2 + \left\| \text{Im}\left\{\hat{h}^{(2)}(v, u)\right\} \right\|^2 \quad (36)$$

$$x_3(v, u) = \text{Re}\left\{\hat{h}^{(1)}(v, u)\right\}^\dagger \text{Im}\left\{\hat{h}^{(1)}(v, u)\right\} + \text{Re}\left\{\hat{h}^{(2)}(v, u)\right\}^\dagger \text{Im}\left\{\hat{h}^{(2)}(v, u)\right\} \quad (37)$$

In more general, the different spatial dimensions of $\hat{h}(v, u)$ can be optimally utilized to obtain the breathing rate. Note that we split $\hat{h}(v, u)$ into 3 components:

$$\hat{h}^{(1)}(v, u) = \frac{\hat{h}(v, u) + \hat{h}(-v, u)^*}{2} \quad (38)$$

$$\hat{h}^{(3)}(v, u) = \left(\mathbf{1}_{MN} - \|\hat{\mathcal{B}}_k\|^{-2}|\hat{\mathcal{B}}_k\|\hat{\mathcal{B}}_k|^\dagger\right)\frac{\hat{h}(v, u) - \hat{h}(-v, u)^*}{2j} \quad (39)$$

$$\hat{h}^{(4)}(v, u) = \|\hat{\mathcal{B}}_k\|^{-2}|\hat{\mathcal{B}}_k\|\hat{\mathcal{B}}_k|^\dagger \frac{\hat{h}(v, u) - \hat{h}(-v, u)}{2j} \quad (40)$$

From the analysis, component $\hat{h}^{(1)}(v, u)$ is affected by the residual AGC gain error $\bar{g}_p$ but is resilient to the residual phase error $\varphi_p$. Similarly, component $\hat{h}^{(4)}(v, u)$ is affected by the residual phase error $\varphi_p$ but is resilient to the AGC gain error $\bar{g}_p$. Finally, component $\hat{h}^{(3)}(v, u)$ is resilient to both the residual AGC gain error $\bar{g}_p$ and the residual phase error $\varphi_p$. Correspondingly in one embodiment, different weights can be assigned to the 3 components $\hat{h}(v, u)$ when estimating the breathing rate.

In the embodiment of Algorithm 4, the estimate of the breathing rate can be obtained as: $\hat{f}_{br} = v_0/(P\,T_{rep})$, where:

$$v_0 = \quad (41)$$
$$\arg\max_{v \in \mathcal{V}_0} \left\{ \sum_{u \in \mathcal{U}_0} w_1 \left\|\hat{h}^{(1)}(v, u)\right\|^2 + w_3 \left\|\hat{h}^{(3)}(v, u)\right\|^2 + w_4 \left\|\hat{h}^{(4)}(v, u)\right\|^2 \right\}$$

The terms $w_1$, $w_3$, $w_4$ are weights assigned to the three components. A similar to embodiment of Algorithm 2, this embodiment of Algorithm 4 enables use of $$\max_{u \in \mathcal{U}_0} \{.\}$$

instead of $\sum_{u \in \mathcal{U}_0}(.)$.

In the embodiment of Algorithm 5, the estimate of the breathing rate can be obtained as: $\hat{f}_{br} = v_0/(P\,T_{rep})$, where:

$$v_0 = \quad (42)$$
$$\arg\max_{v \in \mathcal{V}_0} \left\{ x_{12}(v, u) + x_{22}(v, u) + \sqrt{(x_{12}(v, u) - x_{22}(v, u))^2 + 4x_{32}(v, u)} \right\}$$

$$x_{12}(v, u) = \left\| \text{Re}\left\{\hat{h}^{(12)}(v, u)\right\} \right\|^2 + \left\| \text{Re}\left\{\hat{h}^{(22)}(v, u)\right\} \right\|^2 \quad (43)$$

$$x_{22}(v, u) = \left\| \text{Im}\left\{\hat{h}^{(12)}(v, u)\right\} \right\|^2 + \left\| \text{Im}\left\{\hat{h}^{(22)}(v, u)\right\} \right\|^2 \quad (44)$$

$$x_{32}(v, u) = \quad (45)$$
$$\text{Re}\left\{\hat{h}^{(12)}(v, u)\right\}^\dagger \text{Im}\left\{\hat{h}^{(12)}(v, u)\right\} + \text{Re}\left\{\hat{h}^{(22)}(v, u)\right\}^\dagger \text{Im}\left\{\hat{h}^{(22)}(v, u)\right\}$$

$$\hat{h}^{(12)}(v, u) = w_1 \hat{h}^{(1)}(v, u) \quad (46)$$

$$\hat{h}^{(22)}(v, u) = w_3 \hat{h}^{(3)}(v, u) + w_4 \hat{h}^{(4)}(v, u) \quad (47)$$

The terms $w_1$, $w_3$, $w_4$ are weights assigned to the three components.

In the embodiment of Algorithm 6, the estimate of the breathing rate can be obtained as: $\hat{f}_{br} = v_0/(P\,T_{rep})$, where:

$$v_0 = \quad (48)$$
$$\arg\max_{v \in \mathcal{V}_0} \left\{ x_{13}(v, u) + x_{23}(v, u) + \sqrt{(x_{13}(v, u) - x_{23}(v, u))^2 + 4x_{33}(v, u)} \right\}$$

$$x_{13}(v, u) = \left\| \text{Re}\left\{\hat{h}^{(22)}(v, u)\right\} \right\|^2 \quad (49)$$

$$x_{23}(v, u) = \left\| \text{Im}\left\{\hat{h}^{(22)}(v, u)\right\} \right\|^2 \quad (50)$$

$$x_{32}(v, u) = \text{Re}\left\{\hat{h}^{(22)}(v, u)\right\}^\dagger \text{Im}\left\{\hat{h}^{(22)}(v, u)\right\} \quad (51)$$

$$\hat{h}^{(22)}(v, u) = w_3 \hat{h}^{(3)}(v, u) + w_4 \hat{h}^{(4)}(v, u) \quad (52)$$

and $w_3$, $w_4$ are weights assigned to the two components.

In the embodiment of Algorithm 7, the estimate of the breathing rate can be obtained as: $\hat{f}_{br} = v_0/(P\,T_{rep})$, where:

$$v_0 = \quad (53)$$
$$\arg\max_{v \in \mathcal{V}_0} \left\{ x_{14}(v, u) + x_{24}(v, u) + \sqrt{(x_{14}(v, u) - x_{24}(v, u))^2 + 4x_{34}(v, u)} \right\}$$

$$x_{14}(v, u) = \left\| \text{Re}\left\{\hat{h}^{(14)}(v, u)\right\} \right\|^2 + \left\| \text{Re}\left\{\hat{h}^{(24)}(v, u)\right\} \right\|^2 \quad (54)$$

$$x_{24}(v, u) = \left\| \text{Im}\left\{\hat{h}^{(14)}(v, u)\right\} \right\|^2 + \left\| \text{Im}\left\{\hat{h}^{(24)}(v, u)\right\} \right\|^2 \quad (55)$$

$$x_{34}(v, u) = \quad (56)$$
$$\text{Re}\left\{\hat{h}^{(14)}(v, u)\right\}^\dagger \text{Im}\left\{\hat{h}^{(14)}(v, u)\right\} + \text{Re}\left\{\hat{h}^{(24)}(v, u)\right\}^\dagger \text{Im}\left\{\hat{h}^{(24)}(v, u)\right\}$$

$$\hat{h}^{(14)}(v, u) = w_1 \hat{h}^{(1)}(v, u) \quad (57)$$

$$\hat{h}^{(24)}(v, u) = w_3 \hat{h}^{(3)}(v, u) \quad (58)$$

In the embodiment of Algorithm 8, the components of CSI: $\hat{h}^{(1)}(v, u)$, $\hat{h}^{(3)}(v, u)$, $\hat{h}^{(4)}(v, u)$ can be extracted and fed as inputs to a neural network to generate as an output either $\hat{f}_{br}$ or $v_0$. The neural network can then be trained to perform the regression task of estimating the true breathing rate $f_{br}$ or $v_0$ as the output. For training the network, a large 'labelled' data set can be collected for CSI of subjects, where the ground truth label $f_{br}$ can be obtained using, for example, by attaching a respiration force belt to the subject in each data sample. Regularization of the CSI can be expressed according to Equation 59, which regularization can be performed before computing the 3 components $\hat{h}^{(1)}(v, u)$, $\hat{h}^{(3)}(v, u)$, $\hat{h}^{(4)}(v, u)$ to feed as input to the neural network.

$$\tilde{h}(v, u) = \hat{h}(v, u) \sqrt{\frac{KPMN}{\sum_{v,u} \|\hat{h}(v, u)\|^2}} \quad (59)$$

In some embodiments the receiver 311 may have an algorithmic logic to determine (e.g., select) which of the multiple algorithm options described above to use for breathing rate estimation. For example, such a selection can be based on the level of residual AGC gain error and residual phase error in the compensated CSI, which can be either pre-configured values or can be values calculated from the statistics of the compensated CSI $\{\widetilde{\mathcal{H}}_{0,k}, \ldots, \widetilde{\mathcal{H}}_{P-1,k}\}$.

In some embodiments the estimated breathing rate $\hat{f}_{br}$, Doppler bin $v_0$, and or delay bin $u_0$ can be input into another tracking algorithm, such as a Kalman filter, for further error reduction. In one embodiment the estimate of $\hat{f}_{br}$, $v_0$, $u_0$ can also be saved and used as a priori side-information for future breathing rate estimation iterations. In one embodiment, the confidence in these estimates can also be used to trigger stopping of future iterations of the breathing rate estimation process.

Figure 18:
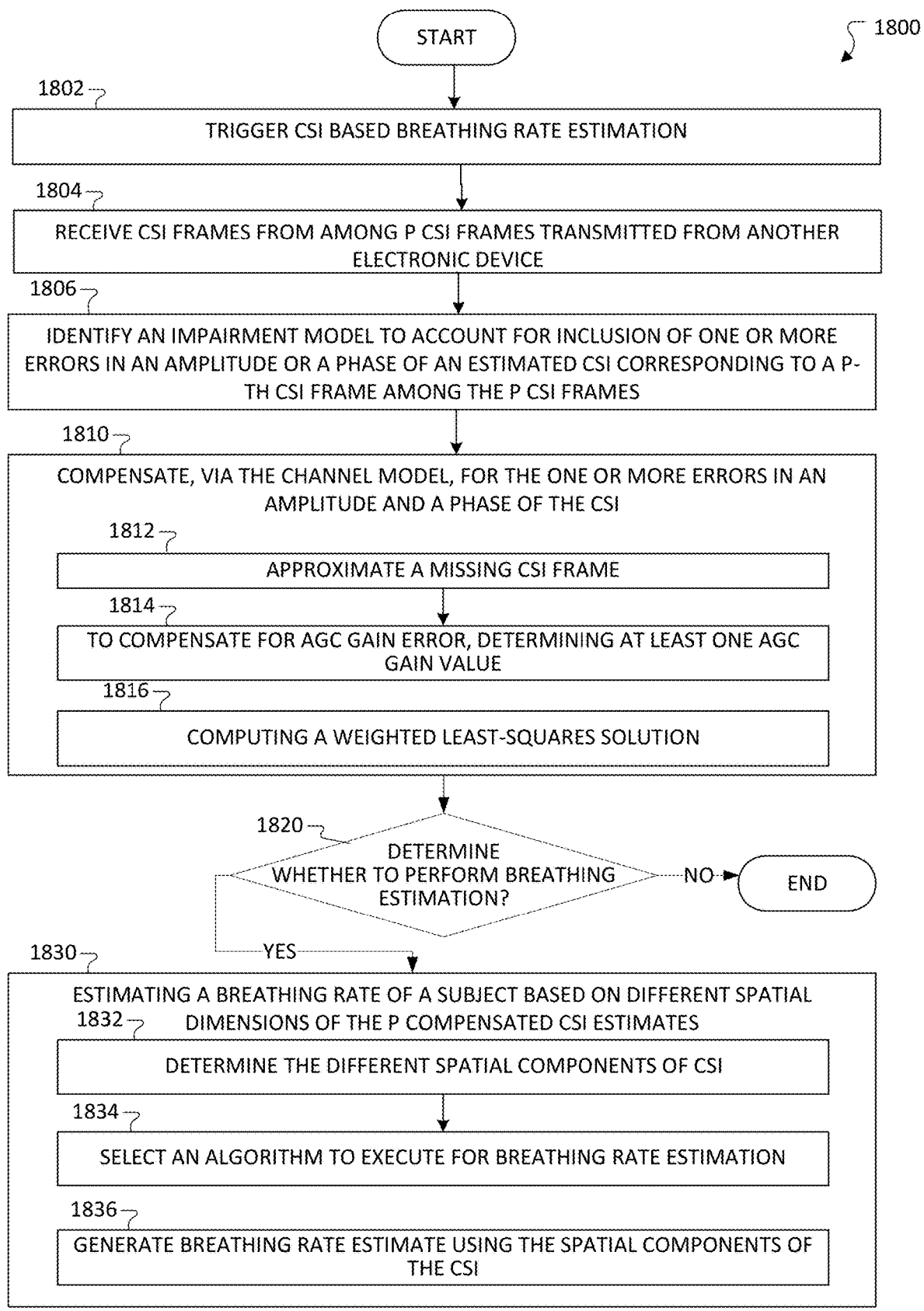
FIG. 18 illustrates a process for estimating a breathing rate based on multi-antenna WiFi signals, in accordance with an embodiment of this disclosure.

FIG. 18 illustrates a method 1800 for estimating a breathing rate based on multi-antenna WiFi signals in accordance with an embodiment of this disclosure. The embodiment of the method 1800 for shown in FIG. 18 is for illustration only, and other embodiments could be used without departing from the scope of this disclosure. The method 1800 for is implemented by an electronic device, such as STA 111 or 311 of FIG. 2B or FIG. 3, respectively. More particularly, the method 1800 for could be performed by a processor 240 of the electronic device executing the computer program includes computer readable program code that when executed causes at least one processor to perform the method 1800 For ease of explanation, the method 1800 is described as being performed by the processor 240 executing one or more application 262.

At block 1802, the processor 240 triggers CSI-based breathing rate estimation. The procedure performed at block 1802 can be the same as the procedure of block 510 of FIG. 5. In one embodiment, the CSI-based breathing rate estimation can be triggered by an external source or a timer. In another embodiment, another algorithm can use the received CSI (e.g., one or more of the CSI frames 402 of FIG. 4)) to trigger the breathing rate estimation. As an example, a sudden and/or significant variation of the CSI $\widetilde{\mathcal{H}}_{p,k}$ compared to its past values can be used to trigger the breathing rate estimation process. As another example, the result of a previous round of breathing rate estimation can be used as a trigger to initiate or stop breathing rate estimation process. In yet another embodiment, the transmitter 301 can trigger the breathing rate estimation process by transmitting a frame (e.g., CSI frame 402) to the receiver 311. In yet another embodiment, the receiver 311 continuously and periodically estimates the breathing rate of a subject without a trigger.

At block 1804, the processor 240 receive channel state information (CSI) frames among P CSI frames transmitted from M transmit (Tx) antennas of another electronic device. For example, the STA 311 receives unprocessed CSI transmitted from the AP 301. The processor 240 is operably connected to a transceiver of the electronic device. In certain embodiments, a multi-antenna STA 311 receives a sequence of P CSI frames 402 transmitted from a multi-antenna AP 301, such that M>1 and N>1. In other embodiments, a multi-antenna STA 311 receives a sequence of P CSI frames 402 transmitted from a transmitter that has single antenna, such that M=1 and N>1. In yet another embodiment, a single antenna STA 311 receives a sequence of P CSI frames 402 transmitted from a transmitter that has a single antenna, such that M=N=1.

At block 1806, the processor identifies an impairment model to account for inclusion of one or more errors in an amplitude or a phase of an estimated CSI that is indexed by p and that corresponds to a p-th CSI frame among the P CSI frames. In some embodiments, to identify the impairment model, the processor 240 identifies the impairment model that includes a combination of static component and a dynamic component, based on an assumption that the dynamic component includes the breathing rate of the subject 380.

At block 1810, the processor 240 compensates, via the impairment model, for the one or more errors in the amplitude and the phase of P CSI estimates. To compensate for the one or more errors in the amplitude and the phase of the P CSI estimates, the processor 240 executes a procedure of at least one of: block 1812, block 1814, or block 1816.

At block 1812, the processor 240 approximates a missing CSI estimate corresponding to a missing CSI frame among P CSI frames based on the available CSI estimates. This approximation compensates for a missing CSI Frame. Embodiments of this disclosure determine the missing CSI estimate corresponding to the missing CSI frame based on a function of multiple available CSI estimates including the preceding and the succeeding available CSI frames. In some embodiments, the processor determines the missing CSI estimate corresponding to the missing CSI frame as equivalent to a preceding available CSI estimate corresponding to a preceding CSI frame that is closest to the missing CSI frame. In some embodiments, the processor determines the missing CSI estimate corresponding to the missing CSI frame as equivalent to a succeeding available CSI estimate corresponding to a succeeding CSI frame that is closest to the missing CSI frame.

At block 1814, the processor 240 determine at least one automatic gain control (AGC) gain value. To determine the at least one AGC gain value, for each of the P CSI estimates, the processor 240 measures a CSI power value for each of MN antenna pairs. The MN antenna pairs are composed from the N Rx antennas respectively paired with each of the M Tx antennas, and each of the MN antenna pairs is indexed by m. For each antenna pair m among the MN antenna pairs, the processor 240 applies a clustering algorithm to the measured CSI power values to identify clusters, thereby identifying W clusters for the antenna pair m. For each of the W clusters identified for the antenna pair m, the processor 240 determines a square-root ($\sqrt{\Gamma_{p,m}}$) of each measured CSI power value within the cluster, and determines an average value of the determined square roots as an AGC gain value ($[\hat{g}_p]_m$) corresponding to the cluster. To generate an AGC gain-compensated CSI ($[\widetilde{\mathcal{H}}_{p,k}]_m$), the processor 240 divides a CSI estimate ($[\widetilde{\mathcal{H}}_{p,k}]_m$) corresponding to the m-the antenna pair by the AGC gain value ($[\hat{g}_p]_m$) corresponding to the cluster.

In some embodiments, to generate an AGC gain-compensated CSI ($[\widetilde{\mathcal{H}}_{p,k}]_m$) for each of the P CSI estimates, the processor 240 measures a CSI power value ($\Gamma_{p,m}$) for each of MN antenna pairs. for each antenna pair m among the MN antenna pairs, determine to compensate for the one or more errors in the amplitude of the respective CSI estimate that is indexed by p among P CSI estimates, based on a determination that a difference between CSI power values measured for consecutive CSI estimates is not exceeded by a threshold value (i.e., $|\Gamma_{p,m} - \Gamma_{p-1,m}| \geq$ Threshold is TRUE). The processor 240 compensates for the one or more errors in the amplitude of the respective CSI frame caused by AGC gain by generating an AGC gain-compensated channel model $([\bar{\mathcal{H}}_{p,k}]_m)$ that is expressed as Equation 9.

In certain embodiments, the processor detects a corrupted CSI estimate based on an outlier threshold and a function of P compensated CSI estimates. The processor 240 removes and/or replaces the corrupted CSI frame (e.g., corrupted CSI sample) within the P compensated CSI estimates.

At block 1816, the processor 240 compute the one or more errors in the phase based on a weighted least-squares solution. More particularly, the processor 240 computes a timing error and the one or more errors in the phase for the p-th CSI estimate as the weighted least-squares solution based on an estimate of a static component of the p-th CSI estimate.

At block 1820, the processor 240 determines whether to perform breathing estimation. In response to a determination to perform breathing estimation, the method proceeds to block 1830.

At block 1830, the processor estimates a breathing rate ($f_{br}$) of a subject 380 based on different spatial dimensions of the P compensated CSI estimates. Block 1830 includes block 1832, 1834, and 1836.

At block 1832, the processor 240 defines different spatial dimensions of the Doppler-delay transformation of the compensated CSI represents the different spatial dimensions of the P compensated CSI estimates. For example, as shown in provided in Equations 30 and 31. In some embodiments, the processor 240 splits the Doppler-delay CSI into different components (e.g., $\hat{h}^{(1)}(v, u)$ and $\hat{h}^{(3)}(v, u)$ and $\hat{h}^{(4)}(v, u)$) that respectively correspond to different spatial sub-dimensions. The different spatial sub-dimensions include: a first spatial sub-dimension in which a first component of the Doppler-delay CSI is affected by a residual AGC gain error and is resilient to a residual phase error; a second spatial sub-dimension in which a second component of the Doppler-delay CSI is affected by the residual phase error and is resilient to the residual AGC gain error; and a third spatial sub-dimension in which a third component of the Doppler-delay CSI is resilient to both the residual AGC gain error and the residual phase error.

At block 1834, the processor 240 selects a breathing rate algorithm from among a plurality of algorithms (e.g., Algorithms 1-8) for estimating the breathing rate, based on a Doppler-delay transformation of the compensated CSI expressed as $\hat{h}(v, u)$. Here, v represents Doppler frequency bin index, and u represents a delay bin index.

At block 1836, the processor 240 generates the breathing rate estimate $f_{br}$ using the spatial components of the CSI and the selected algorithm for estimating the breathing rate. In certain embodiments, to execute the selected breathing rate algorithm, the processor 240 combines signals in each of the first, second, and third spatial sub-dimensions to reduce an impact of the residual AGC gain error and the residual phase error on the estimated breathing rate. In certain embodiments, to execute the selected breathing rate algorithm, the processor 240 identifies different components of the Doppler-delay transformation of the compensated CSI, and assign weights to each of the different components of the Doppler-delay transformation of the compensated CSI.

Although FIG. 18 illustrates an example method 1800 for estimating a breathing rate based on multi-antenna WiFi signals, various changes may be made to FIG. 14. For example, while shown as a series of steps, various steps in FIG. 18 could overlap, occur in parallel, occur in a different order, or occur any number of times. For example, the processor 240 can execute additional steps or functions based on the breathing rate estimated.

The above flowcharts illustrate example methods that can be implemented in accordance with the principles of the present disclosure and various changes could be made to the methods illustrated in the flowcharts herein. For example, while shown as a series of steps, various steps in each figure could overlap, occur in parallel, occur in a different order, or occur multiple times. In another example, steps may be omitted or replaced by other steps.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system.

Although the present disclosure has been described with exemplary embodiments, various changes and modifications may be suggested to one skilled in the art. It is intended that the present disclosure encompass such changes and modifications as fall within the scope of the appended claims. None of the description in this application should be read as implying that any particular element, step, or function is an essential element that must be included in the claims scope. The scope of patented subject matter is defined by the claims.

What is claimed is:

1. A method comprising:
receiving, by a transceiver that includes N receive (Rx) antennas, channel state information (CSI) frames among P CSI frames transmitted from M transmit (Tx) antennas of another electronic device;
estimating, by a processor of an electronic device operably connected to the transceiver, a CSI from each of the received CSI frames as an available CSI estimate;
identifying an impairment model to account for inclusion of one or more errors in an amplitude or a phase of an estimated CSI that is indexed by p and that corresponds to a p-th CSI frame among the P CSI frames;
compensating, via the impairment model, for the one or more errors in the amplitude and the phase of P CSI estimates, wherein the compensating for the one or more errors in the amplitude and the phase of the P CSI estimates includes performing at least one of:
approximating a missing CSI estimate corresponding to a missing CSI frame among P CSI frames based on the available CSI estimates;
determining at least one automatic gain control (AGC) gain value; or
computing the one or more errors in the phase based on a weighted least-squares solution; and
estimating a breathing rate of a subject based on different spatial dimensions of the P compensated CSI estimates.

2. The method of claim 1, wherein further comprising approximating the missing CSI estimate corresponding to the missing CSI frame as one of:
equivalent to a preceding available CSI estimate corresponding to a preceding CSI frame that is closest to the missing CSI frame;

equivalent to a succeeding available CSI estimate corresponding to a succeeding CSI frame that is closest to the missing CSI frame; or based on a function of multiple available CSI estimates including the preceding and the succeeding available CSI frames.

3. The method of claim 1, wherein determining the at least one AGC gain value further comprises:

for each of the P CSI estimates, measuring a CSI power value for each of MN antenna pairs, the MN antenna pairs composed from the N Rx antennas respectively paired with each of the M Tx antennas, each of the MN antenna pairs indexed by m;

for each antenna pair m among the MN antenna pairs, applying a clustering algorithm to the measured CSI power values to identify W clusters; and for each of the W clusters identified:

determining a square-root ($\sqrt{\Gamma_{p,m}}$) of each measured CSI power value within the cluster;

determining an average value of the determined square roots as an AGC gain value ($[\hat{g}_p]_m$) corresponding to the cluster; and dividing a CSI estimate ($[\widetilde{\mathcal{H}}_{p,k}]_m$) corresponding to the m-the antenna pair by the AGC gain value ($[\hat{g}_p]_m$) corresponding to the cluster, thereby generating an AGC gain-compensated CSI ($[\overline{\mathcal{H}}_{p,k}]_m$).

4. The method of claim 1, further comprising:

for each of the P CSI estimates, measuring a CSI power value ($\Gamma_{p,m}$) for each of MN antenna pairs, the MN antenna pairs composed from the N Rx antennas respectively paired with each of the M Tx antennas, each of the MN antenna pairs indexed by m; and for each antenna pair m among the MN antenna pairs, determining to compensate for the one or more errors in the amplitude of the respective CSI estimate that is indexed by p among P CSI estimates, based on a determination that a difference between CSI power values measured for consecutive CSI estimates is not exceeded by a threshold value.

5. The method of claim 1, further comprising:

detecting a corrupted CSI estimate based on an outlier threshold and a function of P compensated CSI estimates; and replacing the corrupted CSI frame within the P compensated CSI estimates.

6. The method of claim 1, further comprising computing a timing error and the one or more errors in the phase for the p-th CSI estimate as the weighted least-squares solution based on an estimate of a static component of the p-th CSI estimate.

7. The method of claim 1, further comprising:

selecting a breathing rate algorithm from among a plurality of algorithms for estimating the breathing rate, based on a Doppler-delay transformation of the compensated CSI expressed as ĥ(v, u), where v represents Doppler frequency bin index, and u represents a delay bin index; and wherein different spatial dimensions of the Doppler-delay transformation of the compensated CSI represents the different spatial dimensions of the P compensated CSI estimates.

8. The method of claim 7, further comprising splitting the Doppler-delay CSI into different components that respectively correspond to different spatial sub-dimensions, including:

a first spatial sub-dimension in which a first component of the Doppler-delay CSI is affected by a residual AGC gain error and is resilient to a residual phase error;

a second spatial sub-dimension in which a second component of the Doppler-delay CSI is affected by the residual phase error and is resilient to the residual AGC gain error; and a third spatial sub-dimension in which a third component of the Doppler-delay CSI is resilient to both the residual AGC gain error and the residual phase error; and wherein executing the selected breathing rate algorithm comprises combining signals in each of the first, second, and third spatial sub-dimensions to reduce an impact of the residual AGC gain error and the residual phase error on the estimated breathing rate.

9. The method of claim 7, wherein executing the selected breathing rate algorithm, further comprises identifying different components of the Doppler-delay transformation of the compensated CSI;

assigning weights to each of the different components of the Doppler-delay transformation of the compensated CSI.

10. The method of claim 1, wherein identifying the impairment model further comprises identifying the impairment model that includes a combination of static component and a dynamic component, based on an assumption that the dynamic component includes the breathing rate of the subject.

11. An electronic device comprising:

a transceiver that includes N receive (Rx) antennas; and a processor operably connected to the transceiver and configured to:

receive channel state information (CSI) frames among P CSI frames transmitted from M transmit (Tx) antennas of another electronic device;

estimate a CSI from each of the received CSI frames as an available CSI estimate;

identify an impairment model to account for inclusion of one or more errors in an amplitude or a phase of an estimated CSI that is indexed by p and that corresponds to a p-th CSI frame among the P CSI frames;

compensate, via the impairment model, for the one or more errors in the amplitude and the phase of P CSI estimates, wherein to compensate for the one or more errors in the amplitude and the phase of the P CSI estimates, the processor is further configured to perform at least one of:

approximate a missing CSI estimate corresponding to a missing CSI frame among P CSI frames based on the available CSI estimates;

determine at least one automatic gain control (AGC) gain value; or compute the one or more errors in the phase based on a weighted least-squares solution; and estimate a breathing rate of a subject based on different spatial dimensions of the P compensated CSI estimates.

12. The electronic device of claim 11, wherein the processor is further configured to approximate the missing CSI estimate corresponding to the missing CSI frame as one of:

equivalent to a preceding available CSI estimate corresponding to a preceding CSI frame that is closest to the missing CSI frame;

equivalent to a succeeding available CSI estimate corresponding to a succeeding CSI frame that is closest to the missing CSI frame; or based on a function of multiple available CSI estimates including the preceding and the succeeding available CSI frames.

13. The electronic device of claim 11, wherein to determine the at least one AGC gain value, the processor is further configured to:
for each of the P CSI estimates, measure a CSI power value for each of MN antenna pairs, the MN antenna pairs composed from the N Rx antennas respectively paired with each of the M Tx antennas, each of the MN antenna pairs indexed by m;
for each antenna pair m among the MN antenna pairs, apply a clustering algorithm to the measured CSI power values to identify W clusters; and
for each of the W clusters identified:
determine a square-root ($\sqrt{\Gamma_{p,m}}$) of each measured CSI power value within the cluster;
determine an average value of the determined square roots as an AGC gain value ($[\hat{g}_p]_m$) corresponding to the cluster; and
divide a CSI estimate ($[\widetilde{\mathcal{H}}_{p,k}]_m$) corresponding to the m-the antenna pair by the AGC gain value ($[\hat{g}_p]_m$) corresponding to the cluster, thereby generating an AGC gain-compensated CSI ($[\overline{\mathcal{H}}_{p,k}]_m$).

14. The electronic device of claim 11, wherein the processor is further configured to:
for each of the P CSI estimates, measure a CSI power value ($\Gamma_{p,m}$) for each of MN antenna pairs, the MN antenna pairs composed from the N Rx antennas respectively paired with each of the M Tx antennas, each of the MN antenna pairs indexed by m; and
for each antenna pair m among the MN antenna pairs, determine to compensate for the one or more errors in the amplitude of the respective CSI estimate that is indexed by p among P CSI estimates, based on a determination that a difference between CSI power values measured for consecutive CSI estimates is not exceeded by a threshold value.

15. The electronic device of claim 11, wherein the processor is further configured to:
identify a magnitude of an AGC gain-compensated CSI estimate ($|\overline{\mathcal{H}}_{p,k}|$) corresponding to each of the P CSI estimates;
identify a mean of magnitude of the P AGC gain-compensated CSI estimates expressed as $\overline{\mathcal{B}}_k = \Sigma_{p \in \mathcal{P}} |\overline{\mathcal{H}}_{p,k}|/P$;
detect a corrupted CSI estimate based on a determination that a comparison is TRUE,
wherein the comparison includes determining whether, for each of K sub-carriers indexed by k, a sum of a squared error between the $|\overline{\mathcal{H}}_{p,k}|$ and the $\overline{\mathcal{B}}_k$ is greater than an outlier threshold; and
replace the corrupted CSI frame within the P compensated CSI estimates.

16. The electronic device of claim 11, wherein the processor is further configured to
compute a timing error and the one or more errors in the phase for the p-th CSI estimate as the weighted least-squares solution based on an estimate of a static component of the p-th CSI estimate.

17. The electronic device of claim 11, wherein the processor is further configured to:
select a breathing rate algorithm from among a plurality of algorithms for estimating the breathing rate, based on a Doppler-delay transformation of the compensated CSI expressed as $\hat{h}(v, u)$, where v represents Doppler frequency bin index, and u represents a delay bin index; and
wherein different spatial dimensions of the Doppler-delay transformation of the compensated CSI represents the different spatial dimensions of the P compensated CSI estimates.

18. The electronic device of claim 17, wherein the processor is further configured to split the Doppler-delay CSI into different components that respectively correspond to different spatial sub-dimensions, including:
a first spatial sub-dimension in which a first component of the Doppler-delay CSI is affected by a residual AGC gain error and is resilient to a residual phase error;
a second spatial sub-dimension in which a second component of the Doppler-delay CSI is affected by the residual phase error and is resilient to the residual AGC gain error; and
a third spatial sub-dimension in which a third component of the Doppler-delay CSI is resilient to both the residual AGC gain error and the residual phase error; and
wherein to execute the selected breathing rate algorithm, the processor is further configured to combine signals in each of the first, second, and third spatial sub-dimensions to reduce an impact of the residual AGC gain error and the residual phase error on the estimated breathing rate.

19. The electronic device of claim 17, wherein to execute the selected breathing rate algorithm, the processor is further configured to:
identify different components of the Doppler-delay transformation of the compensated CSI;
assign weights to each of the different components of the Doppler-delay transformation of the compensated CSI.

20. The electronic device of claim 11, wherein to identify the impairment model, the processor is further configured to identify the impairment model that includes a combination of static component and a dynamic component, based on an assumption that the dynamic component includes the breathing rate of the subject.

* * * * *